United States Patent
Davey et al.

(10) Patent No.: US 10,950,332 B2
(45) Date of Patent: *Mar. 16, 2021

(54) TARGETED SENSATION OF TOUCH

(71) Applicants: Neil Davey, Gaithersburg, MD (US);
Sonya Davey, Gaithersburg, MD (US);
Samir Devalaraja, Waltham, MA (US);
Sanjay Kunchakarra, Clarksville, MD (US)

(72) Inventors: Neil Davey, Gaithersburg, MD (US);
Sonya Davey, Gaithersburg, MD (US);
Samir Devalaraja, Waltham, MA (US);
Sanjay Kunchakarra, Clarksville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/437,182

(22) Filed: Jun. 11, 2019

(65) Prior Publication Data

US 2019/0295699 A1    Sep. 26, 2019

Related U.S. Application Data

(63) Continuation of application No. 15/824,662, filed on Nov. 28, 2017, now Pat. No. 10,319,472, which is a continuation of application No. 13/798,745, filed on Mar. 13, 2013, now Pat. No. 9,830,423.

(51) Int. Cl.
| | |
|---|---|
| *H04B 3/36* | (2006.01) |
| *G16H 10/60* | (2018.01) |
| *G06F 19/00* | (2018.01) |
| *G16H 50/20* | (2018.01) |
| *G16H 40/67* | (2018.01) |

(52) U.S. Cl.
CPC .......... *G16H 10/60* (2018.01); *G06F 19/3418* (2013.01); *G16H 40/67* (2018.01); *G16H 50/20* (2018.01)

(58) Field of Classification Search
CPC ........ G16H 10/60; G16H 40/67; G16H 50/20; G16H 19/3418
USPC ...................................................... 340/407.1
See application file for complete search history.

(56) References Cited

U.S. PATENT DOCUMENTS

| | | | | |
|---|---|---|---|---|
| 4,928,690 A | * | 5/1990 | Heilman | A61B 5/6831 600/509 |
| 5,694,939 A | * | 12/1997 | Cowings | A61B 5/486 600/484 |
| 5,911,687 A | * | 6/1999 | Sato | G06F 19/324 600/300 |
| 7,663,648 B1 | * | 2/2010 | Saldanha | G06T 17/00 345/630 |

(Continued)

*Primary Examiner* — Zhen Y Wu
(74) *Attorney, Agent, or Firm* — Raj S. Dave; Dave Law Group LLC

(57) ABSTRACT

A system comprising a pair of devices to enable communication between a first person and a second person; a body-suit to be worn by the first person; and a model replica of the body-suit configured to receive the tactile stimuli and/or the electrical stimuli from the second person and to convert the tactile stimuli and/or the electrical stimuli into the electrical signals which are conveyed to the body-suit over a network; wherein the body-suit is configured to replicate the tactile stimuli and/or the electrical stimuli of the model replica and convey the tactile stimuli and/or the electrical stimuli to the first person; and wherein the system allows a human to send a physical sensation of touch remotely to another human.

18 Claims, 19 Drawing Sheets

INTERACTION BETWEEN PEOPLE FROM DIFFERENT PLATFORMS

(56) References Cited

U.S. PATENT DOCUMENTS

| | | | |
|---|---|---|---|
| 8,294,557 B1* | 10/2012 | El Saddik | G06F 3/016 340/407.1 |
| 2002/0085724 A1* | 7/2002 | Grasfield | H04M 11/06 381/67 |
| 2003/0037063 A1* | 2/2003 | Schwartz | G06Q 40/08 |
| 2003/0078193 A1 | 4/2003 | Yoneda et al. | |
| 2003/0204563 A1* | 10/2003 | Oka | A61B 5/411 709/203 |
| 2004/0142045 A1* | 7/2004 | Harris | A61K 33/06 424/646 |
| 2005/0012485 A1* | 1/2005 | Dundon | G06F 3/011 318/568.11 |
| 2006/0179022 A1* | 8/2006 | Holland | G06N 3/004 706/45 |
| 2007/0063849 A1* | 3/2007 | Rosella | A41D 1/002 340/573.1 |
| 2007/0130676 A1* | 6/2007 | Von Blucher | A62B 17/006 2/456 |
| 2008/0188777 A1 | 8/2008 | Bedziouk et al. | |
| 2009/0234198 A1* | 9/2009 | Vorse | A61B 5/0002 600/301 |
| 2010/0114263 A1* | 5/2010 | Pressler | A61N 5/0621 607/88 |
| 2010/0305909 A1* | 12/2010 | Wolper | G06T 17/00 703/1 |
| 2011/0066042 A1* | 3/2011 | Pandia | A61B 5/029 600/484 |
| 2011/0148607 A1* | 6/2011 | Zeleny | A41D 13/0015 340/407.1 |
| 2011/0166887 A1* | 7/2011 | Gotlib | G06F 19/3418 705/3 |
| 2011/0263946 A1* | 10/2011 | el Kaliouby | A61B 5/1128 600/300 |
| 2012/0022415 A1* | 1/2012 | Mullen | A61H 9/0078 601/150 |
| 2012/0038739 A1* | 2/2012 | Welch | H04N 13/388 348/14.01 |
| 2012/0078062 A1* | 3/2012 | Bagchi | G06F 16/93 600/300 |
| 2012/0101844 A1* | 4/2012 | Darazs | G06F 19/324 705/2 |
| 2012/0139828 A1* | 6/2012 | Lok | G09B 7/00 345/156 |
| 2012/0165615 A1* | 6/2012 | Choi | A61B 5/0013 600/300 |
| 2012/0209145 A1* | 8/2012 | Grigoriev | A61B 5/221 600/587 |
| 2012/0263381 A1* | 10/2012 | Yoshida | G06F 3/03545 382/189 |
| 2012/0270197 A1* | 10/2012 | Brost | G09B 23/30 434/267 |
| 2012/0284003 A1* | 11/2012 | Gosh | A61B 5/0452 703/2 |
| 2012/0290976 A1* | 11/2012 | Lahm | G06T 19/00 715/810 |
| 2013/0198625 A1* | 8/2013 | Anderson | G06F 3/016 715/701 |
| 2013/0209971 A1* | 8/2013 | Luecke | G06Q 10/10 434/127 |
| 2014/0046692 A1* | 2/2014 | Minter | G16H 80/00 705/3 |
| 2014/0074454 A1* | 3/2014 | Brown | G16H 10/60 704/9 |
| 2014/0180036 A1* | 6/2014 | Bukkapatnam | A61B 5/4818 600/301 |
| 2014/0243608 A1* | 8/2014 | Hunt | G01N 33/6893 600/300 |
| 2018/0082028 A1* | 3/2018 | Davey | G06F 19/3418 |

* cited by examiner

CLOSE FRIENDS. The picture which is showing maximum prominence shows that , this friends is in your need because of being in a situation of emotional extreme

*FIG. 6*

TARGETED SENSATION OF TOUCH

CROSS-REFERENCE TO RELATED APPLICATIONS

The present application is a continuation application of U.S. patent application Ser. No. 15/824,662, filed Nov. 28, 2017 (Now U.S. Pat. No. 10,319,472, Issued on Jun. 11, 2019), which is a continuation application of U.S. patent application Ser. No. 13/798,745, filed Mar. 13, 2013 (Now U.S. Pat. No. 9,830,423, Issued on Nov. 28, 2017), and is incorporated in its entirety herewith.

BACKGROUND

According to International Data Corporation (IDC), a global provider of market intelligence, video communications is one of the most promising industries with the potential to create a market of at least 150 million people in America alone in the next five years.

Certain video communication platforms for groups of individuals to create and share information, interact with each other through the software and generally use the software to achieve an individual or group objective are currently available. Generally, these systems store the collaboration for future reference and further discussion or collaboration. However, these systems have several limitations that have been addressed herein. Also, novel solutions for these limitations are provided herein.

SUMMARY

The embodiments herein relate to a method of establishing a collaborative platform comprising performing a collaborative interactive session for a plurality of members, and analysing affect and cognitive features of some or all of the plurality of members.

In one embodiment, some or all of the plurality of members from different human interaction platforms interact via the collaborative platform, One embodiment can further comprise displaying of targeted advertisements or notifications based on the context of the interactive collaborative session.

One embodiment can further comprise measuring effectiveness of the displaying of targeted advertisements or notifications.

One embodiment can further comprise integrating an application or a device within the collaborative interactive session.

Another embodiment relates to a computer implemented system comprising: a storage medium configured to store a collaborative interactive session data; and a processor configured to perform a collaborative interactive session for a plurality of members, wherein the system analyses affect and cognitive features of some or all of the plurality of members.

In one embodiment, some or all of the plurality of members from different human interaction platforms interact via the collaborative interactive session, wherein the different human interactions platforms comprise social media platforms.

In one embodiment, the system is further configured to display targeted advertisements or notifications based on the context of the interactive collaborative sessions.

In one embodiment, the system is further configured to measure effectiveness of the displaying of targeted advertisements or notifications.

In one embodiment, the system is further configured to integrate an application or a device within the collaborative interactive session.

In one embodiment, the system comprises a sound and/or video hub, wherein the sound and/or video hub allows any member of the plurality of the members to play a song and/or a video and simultaneously allows some or all of the plurality of members to listen and/or watch the song and/or the video played.

In one embodiment, the system comprises audio and/or video synopsis of the collaborative interactive session for the plurality of members using a sound and image-processing technology that creates a summary of an original full-length audio and/or video.

Another embodiment relates to a tangible non-transitory computer readable medium comprising computer executable instructions executable by one or more processors for establishing a collaborative platform comprising performing a collaborative interactive session for a plurality of members, and analyzing affect and cognitive features of some or all of the plurality of members.

In one embodiment, some or all of the plurality of members interact from different human interaction platforms.

One embodiment could further comprise computer executable instructions executable by one or more processors for displaying of targeted advertisements or notifications based on the context of the interactive collaborative sessions.

Embodiments herein relate to a system comprising: a first communication device configured to present data to and/or receive data from a health care practitioner; a second communication device configured to present data to and/or receive data from a patient, which could be a human or animal; a processor configured to determine values of one or more metrics that characterize the patient's mental state based data received from the patient via the second communication device; a storage configured to store the metrics.

In one embodiment, the storage is configured to store long term health data of the patient.

In one embodiment, the storage is configured to store short term health data of the patient.

In one embodiment, the data received from the patient comprise a video.

In one embodiment, the data received from the patient comprise a sound.

In one embodiment, the data received from the patient comprise a drawing or handwriting.

In one embodiment, the data received from the patient comprise communication from the patient to another patient.

In one embodiment, the data received from the patient comprise physical characteristics measured from the patient in real-time.

In one embodiment, the data received from the patient comprise the patient's facial expression.

In one embodiment, the data received from the patient comprise the patient's pupillary dilation.

In one embodiment, the data received from the patient comprise the patient's performance in a game.

In one embodiment, the storage comprises a knowledge base.

Another embodiment relates to a method of diagnosing a patient, which could be a human or animal, the method comprising: collecting data conveying information about symptoms experienced by the patient; storing the data conveying information about symptoms in a database on a virtual communication platform; generating keywords conveying symptoms experienced by the patient; and performing a federated search to obtain a diagnosis of the patient's disease condition, wherein a federated search comprises searching through a database compiled on the virtual communication platform correlating symptoms to disease conditions obtained from a virtual communication platform.

In one embodiment, the keywords are generated using data collected from the virtual communication platform.

One embodiment further comprised monitoring vital signs of the patient over a pre-determined period of time following the diagnosis and logging the data on the virtual communication platform.

In one embodiment, the vital signs comprise one or more of height, weight, heartrate, variation in heart-rate, blood glucose level, and blood pressure.

In one embodiment, the vital signs are monitored using sensors embedded in a body-suit or jacket worn by the patient.

In one embodiment, the body-suit or jacket is configured to provide mechanical and/or electrical stimuli to a part of the patient's body covered by the body-suit or jacket.

In one embodiment, the body-suit or jacket is further configured to be controlled remotely using a using a computer.

In one embodiment, the body-suit or jacket worn by the patient is connected to a model replica of the body-suit available at a remote location.

In one embodiment, the model replica of the body-suit is configured to receive tactile stimuli and convey the tactile stimuli through a connection to the body-suit or jacket worn by the patient.

In one embodiment, the body-suit is configured to replicate the tactile stimuli received through the connection from the model replica and convey the tactile stimuli to the patient wearing the body-suit.

Another embodiment relates to a system for providing tactile and/or electrical stimuli remotely, the system comprising: a body-suit to be worn by a human or animal, the body-suit comprising one or more actuators configured to convert electrical signals to tactile and/or stimuli, wherein the body-suit is configured to convey the tactile and/or electrical stimuli to a body part of the human or animal; a model replica of the body-suit configured to receive tactile stimuli from a human or animal and convert the tactile stimuli into electrical signals capable of being parsed by a computer, wherein the model replica is available at a location remote from the patient, wherein the model replica and the body-suit are connected over a network configured to convey the electrical signals from the model-replica to the body-suit.

In one embodiment, the body-suit is configured to cover one or more of arms, torso, neck, throat, legs, hands and feet of the human.

In one embodiment, the body-suit and the model replica each are connected to one or more computers.

In one embodiment, the one or more computers connected to each of the body-suit and the model replica are connected through the Internet.

In one embodiment, the body-suit is configured to replicate tactile stimuli received by the model replica and convey the tactile stimuli to the human.

In one embodiment, the model-replica is a virtual model of human.

In one embodiment, the body-suit is configured to provide electrical stimuli to the human based on signals received from the virtual model.

In one embodiment, the body-suit comprises sensors configured to generate output signals in response to movement by the human.

In one embodiment, the body-suit is further configured to convey the output signals to the model replica.

In one embodiment, the model replica is configured to convert the output signals received from the body-suit into tactile stimuli.

The foregoing summary is illustrative only and is not intended to be in any way limiting. In addition to the illustrative aspects, embodiments, and features described above, further aspects, embodiments, and features can become apparent by reference to the drawings and the following detailed description.

BRIEF DESCRIPTION OF THE FIGURES

FIG. 6 shows an embodiment of a virtual classroom with e-material used as learning medium, based on study of eye movement, pupillary dilation and facial study.

DETAILED DESCRIPTION

Large amount of online media that is transferred is merged providing convenience to user. This data is analysed to find out affect and cognitive state. Utilising this data, a new form of social interaction platform is developed which will incorporate many features of real human interaction.

The term "affect" refers to the experience of feeling or emotion. Affect is a part of the process of an organism's interaction with stimuli. The word also includes affecting display, which is a facial, vocal, or gestural behavior that serves as an indicator of affect.

The term "cognitive state" refers to the state of exploring internal mental processes, for example, to study how people perceive, remember, think, speak, and solve problems.

SWAP is the acronym of an embodiment of a virtual communication platform system described herein. SWAP and a virtual communication platform system are used synonymously in this application.

Embodiments herein relate to SWAP, which can be a web-based application that serves as a multi-dimensional platform for peer-to-peer communication. Current video communication services such as Skype only provide basic face-to-face contact pathways—the interaction is limited to text, audio, and video. SWAP integrates collaboration with communication. It streamlines the base services of peer-to-peer text, audio and video communication with interaction on various collaborative platforms as well as with individual web-based activity. SWAP can incorporate existing streams of social media.

SWAP strives to be the global leader in providing a unified collaboration platform using Internet communication media while enhancing the capabilities of virtual interaction of people from all walks of life. SWAP can provide young adults with a video communications application that integrates multiple streams of online media with virtual interaction. SWAP can provide a unified platform that allows users of any social media service, such as Facebook or Google+, to interact on, removing the fragmentation within social media communication. This platform also combines text, audio, and video communication with collaboration in the areas of academia, music, and recreational activities such as gaming, extending the capabilities of current virtual communication.

This application can be organized into several spheres of interaction known as "globes". Each globe can provide a base interaction for multiple users to collaborate. Our application can integrate these collaboration platforms with a video feed to enhance overall virtual interaction.

Figure 1:
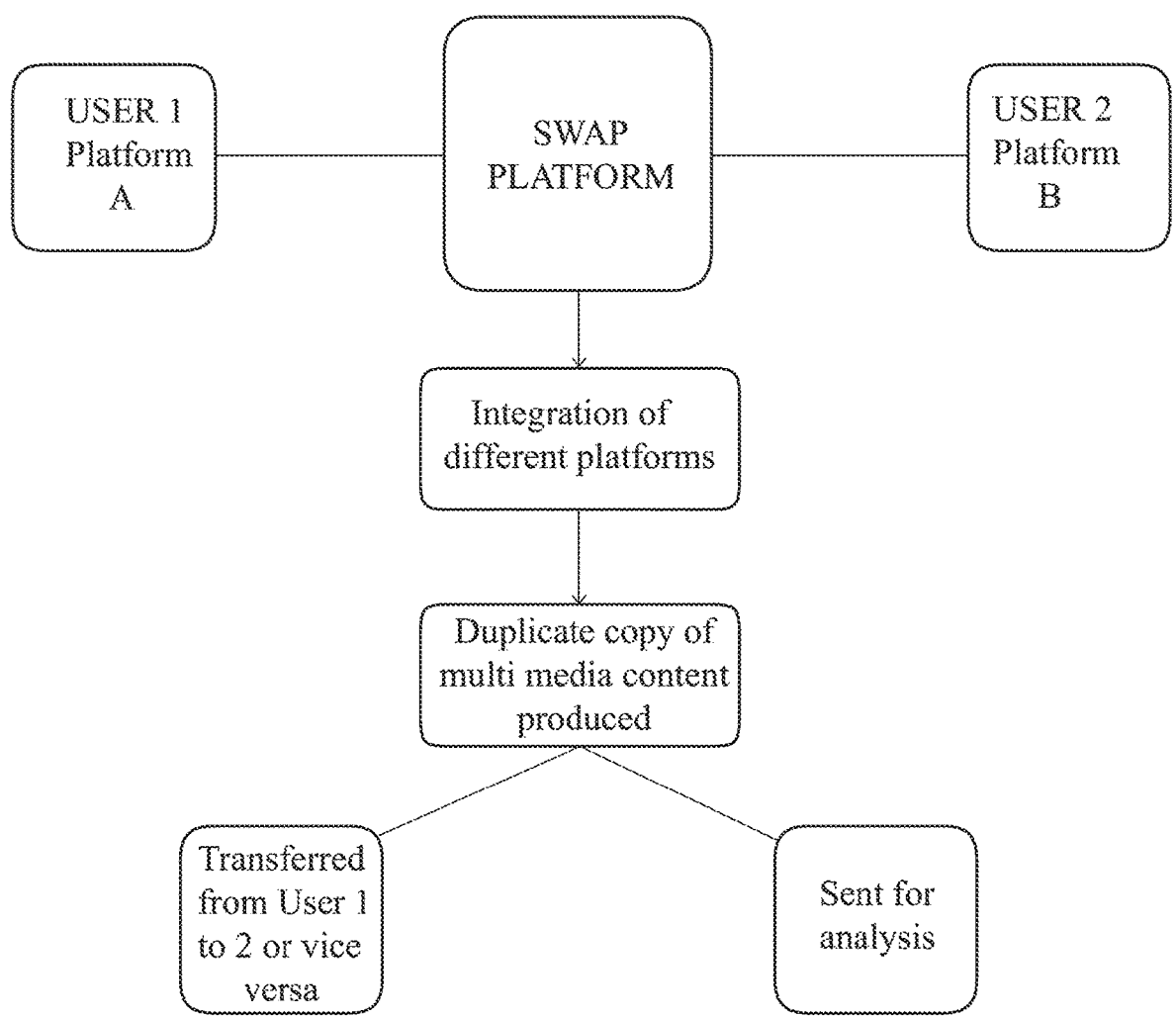
FIG. 1 shows an embodiment of data passing through the SWAP platform, wherein data is acquired and the multimedia segmented and analysed.

The data passing through the SWAP platform will be acquired and the multimedia will be segmented and analysed. This can be seen in FIG. 1. FIG. 1 depicts the SWAP platform that solves the problem of fragmentation and provides a seamless connection between users from separate platforms. These two separate platforms are integrated by SWAP. Interactions between User 1 and User 2 are then sent for analysis. These interactions are used in the Swap+ Profile, Elearning, and SWAP Project.

The derived information from analysis such user emotion and mental states will be utilised in functioning of 3 major SWAP features—
1. Profiles (SWAP+)
2. Targeted Advertisement
3. Smart ELearning (addition to the chalkboard and virtual classroom globe)

SWAP+ Profiles

The way most social networking sites function, they mainly act as a great platform for data storage, sharing and communication. But they these are all a far cry from true social interaction simulation in other words in no way are these anywhere near how we interact in society. Thus the profiles of SWAP+ will be a system which will be much closer to how we remember people, conversations and moreover how we forget. The large amount of data that get passed through the SWAP platform will be analyzed and this data will be used to shape the SWAP+ profiles. The way other people's SWAP+ profiles will appear to us. In this area we try to mimic the way in which we remember people. The profile's emotion feel will be the general emotion that we generally exhibit when we communicate that with that person through any form of media (video, text or speech) (obtained from analyzed data from conversations taking place). Keeping in trend with how we remember people in reality, since how a person is seen by is strongly shaped with event and experiences we share with that person. The profile of the person will bear events, having strong emotions behind them. Any sort media—like text, speech, video or pictures. Texts can be presented simply as they are, videos will we presented like snapshots with the option to be played by the user.

Figure 2:
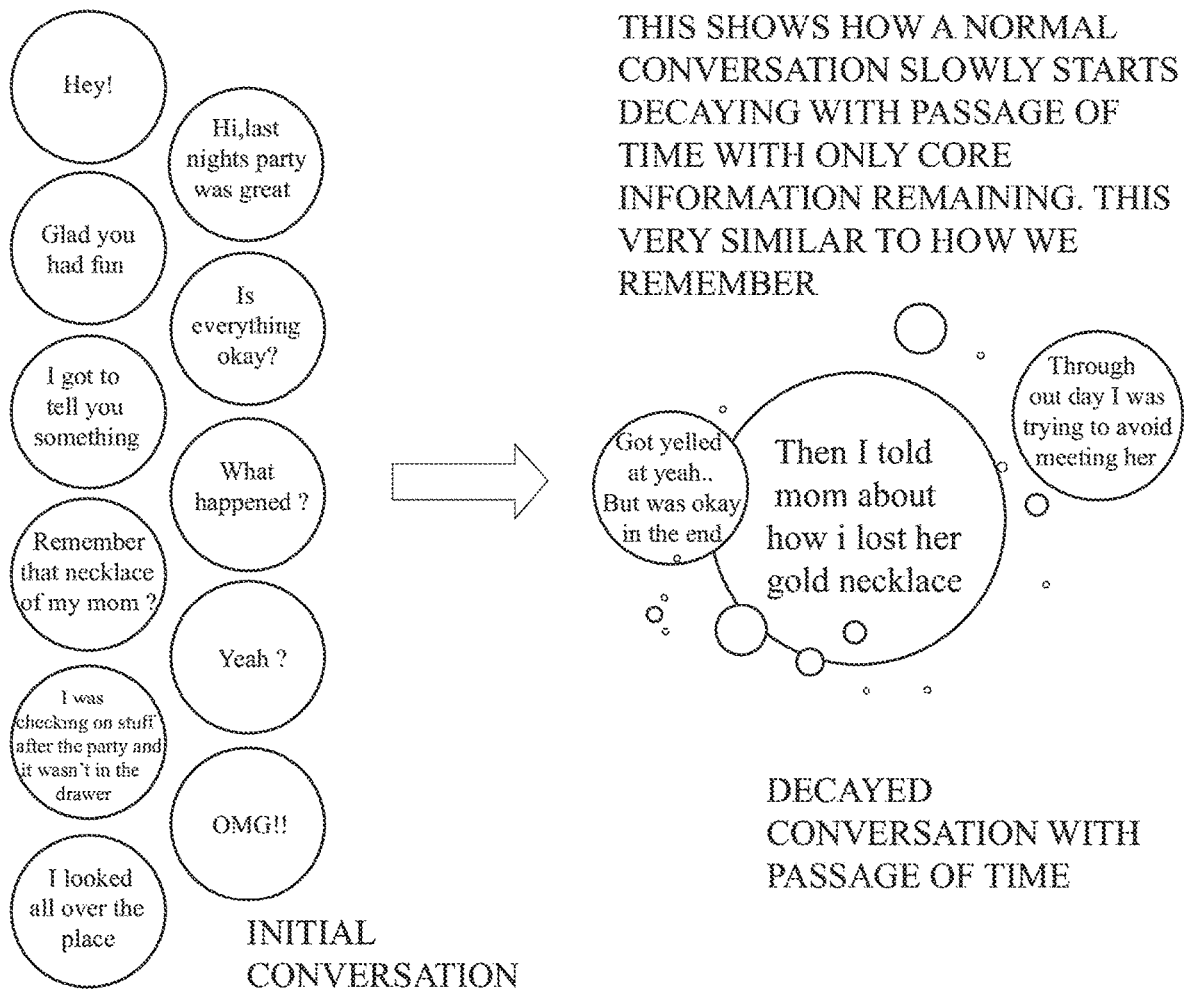
FIG. 2 shows an embodiment of chatting threads.
Figure 3:
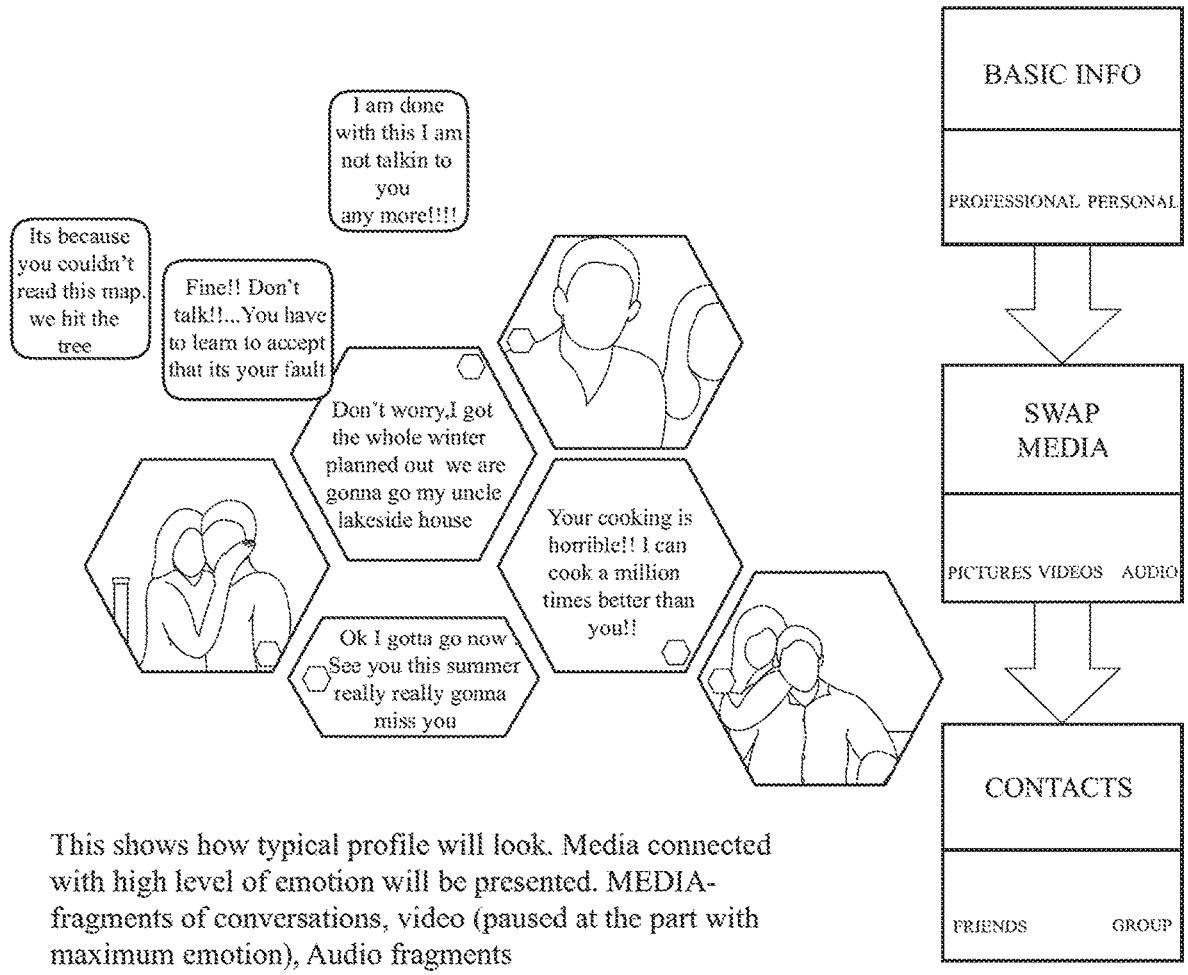
FIG. 3 shows an embodiment of profile appearance.
Figure 4:
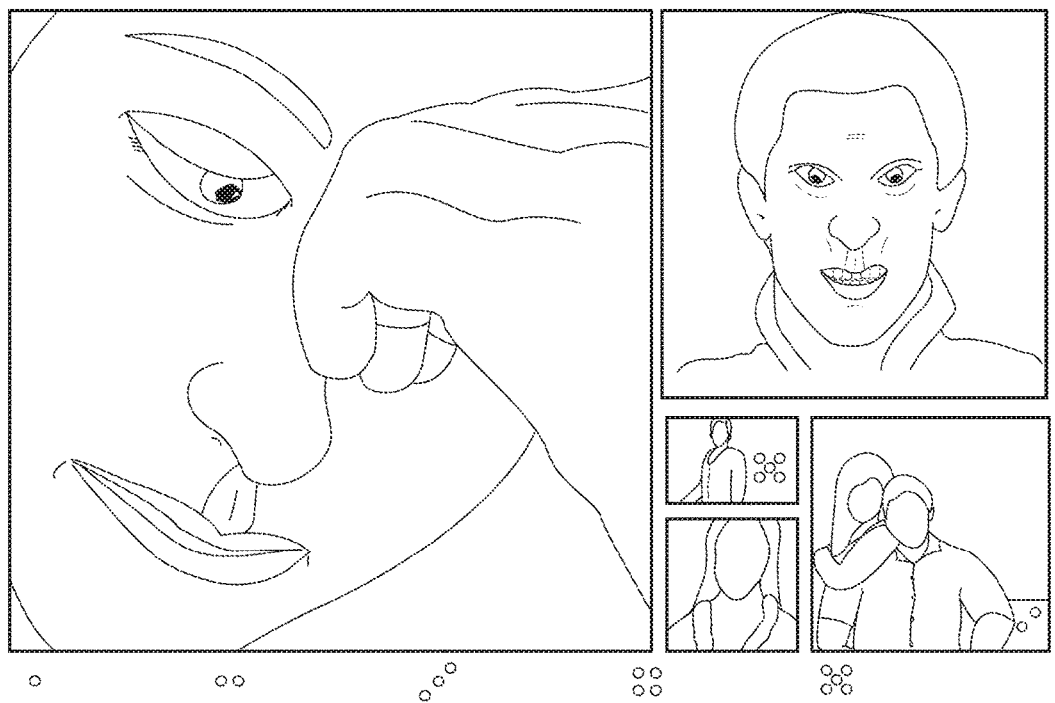
FIG. 4 shows an embodiment of the analysis of data through SWAP for 'close friends'.

The SWAP+ profile can include:
1. Chatting threads (as depicted by FIG. 2)
2. Profile appearance (as depicted by FIG. 3)
3. Close friends (as depicted by FIG. 4)

1. Chatting Threads

The basic flaw which makes social interactions unrealistic is that every bit of data is remembered, unlike the case in real-life daily interactions. To replicate these communications that will be happening through SWAP+ will follow a similar pattern. The comments of the thread will slow start to deteriorate i.e. fade away. The period after which the part of the thread is completely forgotten will be a sort of threshold time, which will be close to average human being time for memory retaining. Memories having high cognitive strain or emotion attached will have much higher threshold time.

In FIG. 2, the comments of the thread will slow start to deteriorate i.e. fade away. The period after which the part of the thread is completely forgotten will be a sort of threshold time, which will be close to average human being time for memory retaining. Memories having high cognitive strain or emotion attached will have much higher threshold time. This example shows a conversation between two friends discussing "last night's party." The initial conversation contains low emotionally attached or insignificant conversation (e.g. "Hey!" "What happened?" "Yeah?"). In the decayed conversation, however such aspects of the conversation are decayed into visually smaller bubbles. The larger bubbles include phrases associated with high cognitive strain or emotion attached. In this example, one friend tells the other "I told mom about how I lost her gold necklace." This phrase is the largest bubbles, assuming that the friend was experiencing significant emotion—including perhaps anxiety, fear, etc.

2. Profile Appearance

In FIG. 3, the profile of SWAP+ will be dynamic in nature constantly changing reflecting the mental state of the user. The real-time mental state will be determined from the various analysis methods, which will be applied on the data passing through SWAP. Under a state of extreme emotion such as depression the user profile will be able to reflect this state. This will allow for other people to be notified of the user's emotional state and hence help him get back normalcy through communication. Through analysis 'close friends' can also be identified who under the above-mentioned situation will be notified. In this example, we see Abhishek Biswas' profile as seen by his girlfriend. Note: this profile is individualized. His girlfriend can see all the important conversations between them (as "decayed conversation" feature.) These conversations include highly emotional both positive and negative phrases. Also, highly emotional paused scenes from videos will appear as well as pictures that have been discussed in emotional conversations.

3. Close Friends

FIG. 4 demonstrates the analysis of data through SWAP for 'close friends'. The analysis will allow the application to identify people with whom the user has discussions of high emotional content. A database of sorts can be created which will store people with whom the user has discussion of high emotional content such as high positive emotion content, high negative emotion content, people with whom through communication emotion changes from negative to positive. Also, people with whom there isn't communication of high emotion content but volume and frequency of communication is very high, these people will also be identified as 'close friends'. Whenever the user is in a state of emotional extreme then the user's profile will be highlighted in the homepages of the 'close friends'. In this example, the friend whose profile shows high levels of distress is the largest. The user can visually identify this friend and try to help her. The second largest picture is also a friend who is visually distressed (which is seen through emotions detected on his profile) and is therefore seen as a large image. The third largest image is the user's girlfriend's profile. Although her profile does not show high emotional context, her profile image is highlighted because of the high volume and frequency of communication.

E-learning

In virtual classroom or chalkboard feature the user may be required to go through leaning material or modules and solve problems. Based on observation of Pupil dilation the cognitive load on user's mind can be found out. If the user is under high cognitive stress for prolonged period it is indicative that the user is unable to make progress with current material or problem. Hence more comprehensive material may be provided and in case problems a hint or a different problem may be provided. Similarly, the pupil study may also indicate the course and problems may not cause appreciable cognitive strain so in this case a course which is less comprehensive and problems of higher difficulty may be presented. The SWAP feature will allow people from different video communication platforms to join into a virtual classroom. This virtual classroom will allow for multiple people to join at same time the course being taught will customized for each individual user. Thus, student gets all the benefits of study in a classroom such discussion, debating, interactive doubt clearance, observing point of view of peers. At the same time the course is modified as peer the learning capacity and mental level of each individual student. So as the all students join the virtual classroom, they all start out with the same course material and as they carry forward with class, constantly each student cognitive load level, attention, stress is being monitored. And based on this data material is modified that will enable maximum learning will be provided. Apart from pupillary dilation and video analysis of face, eye tracking will allow monitoring the movement of the eyes hence it will be possible to see whether that user is being able to focus on the material. Using eye tracking technology we can find the place where the user is looking at and pattern recognition can be utilized to find whether the material being presented is being read or not for example regularized movement of eyes indicate that the user is following the material presented and whereas wandering and random movement of eyes are indicative that the material is not being followed.

The virtual classroom element of SWAP will have advanced tools to simulate real classroom like environment. The nature learning may be of 2 types; video lecture and course material.

Figure 5:
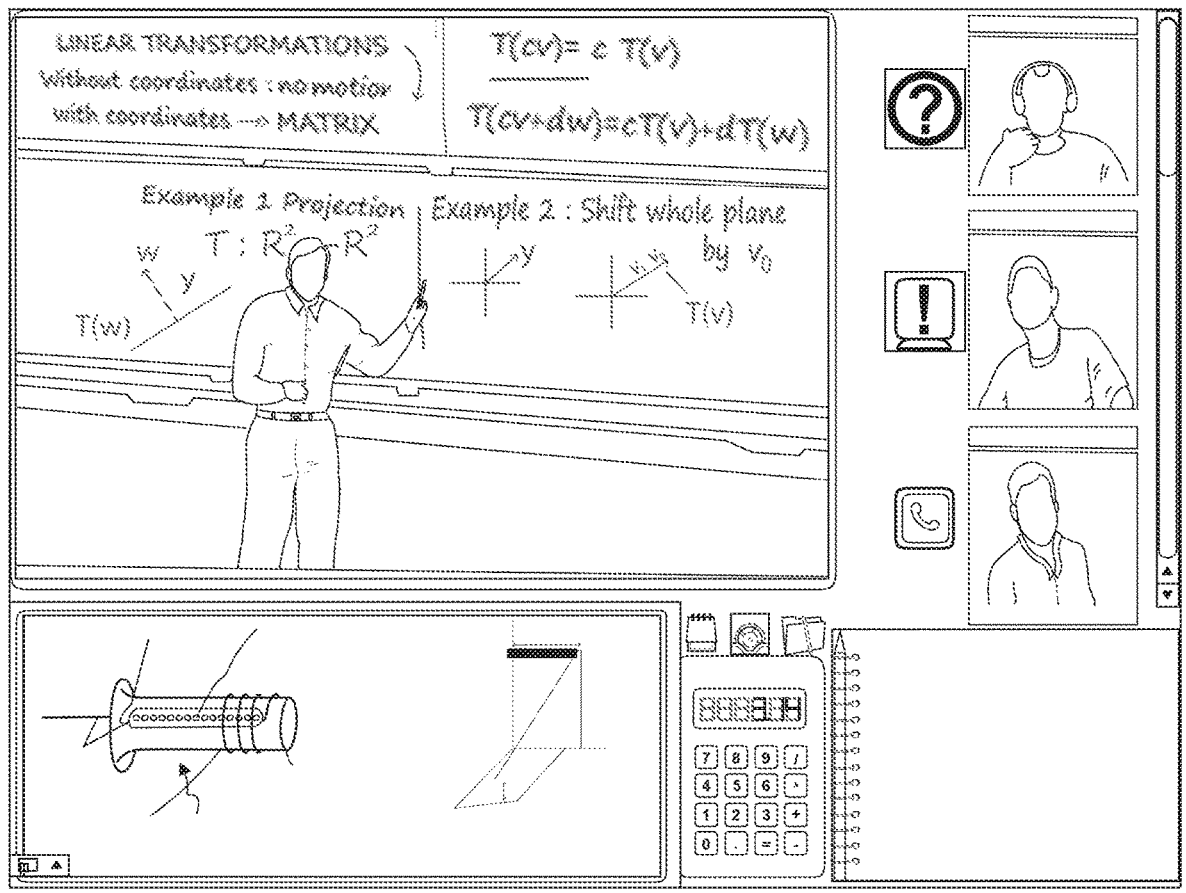
FIG. 5 shows an embodiment of e-learning showing an user interface for studying from a video lecture.

FIG. 5 shows the user interface for studying from video lecture. The following features are present: a notepad where the user can take rough notes, inventory of study aids (like calculator), formula manual (for the course being studied), and access to all rough notes. The work area contains questions and problems that will be asked to the user as each sub segment of the video lecture is completed for those of who finish the problems quickly more problems will be asked and the next sub segment may start only after the minimum number of questions has been completed by everyone. The user will be able to communicate with his other peers and ask them for help or doubt clearance (similar to real classrooms). The feature will also be provided that allows for person who is communicating with user to share his work sheet and help in solving and understanding the problem. As can be seen in this example, the lecture is synchronized with the notes in the formula manual being displayed. Also, based on eye movement, pupillary dilation and facial study of other peers, the student (or teacher) can detect the amount of difficulty or ease his/her peers is having with the class and the problems.

Figure 6:
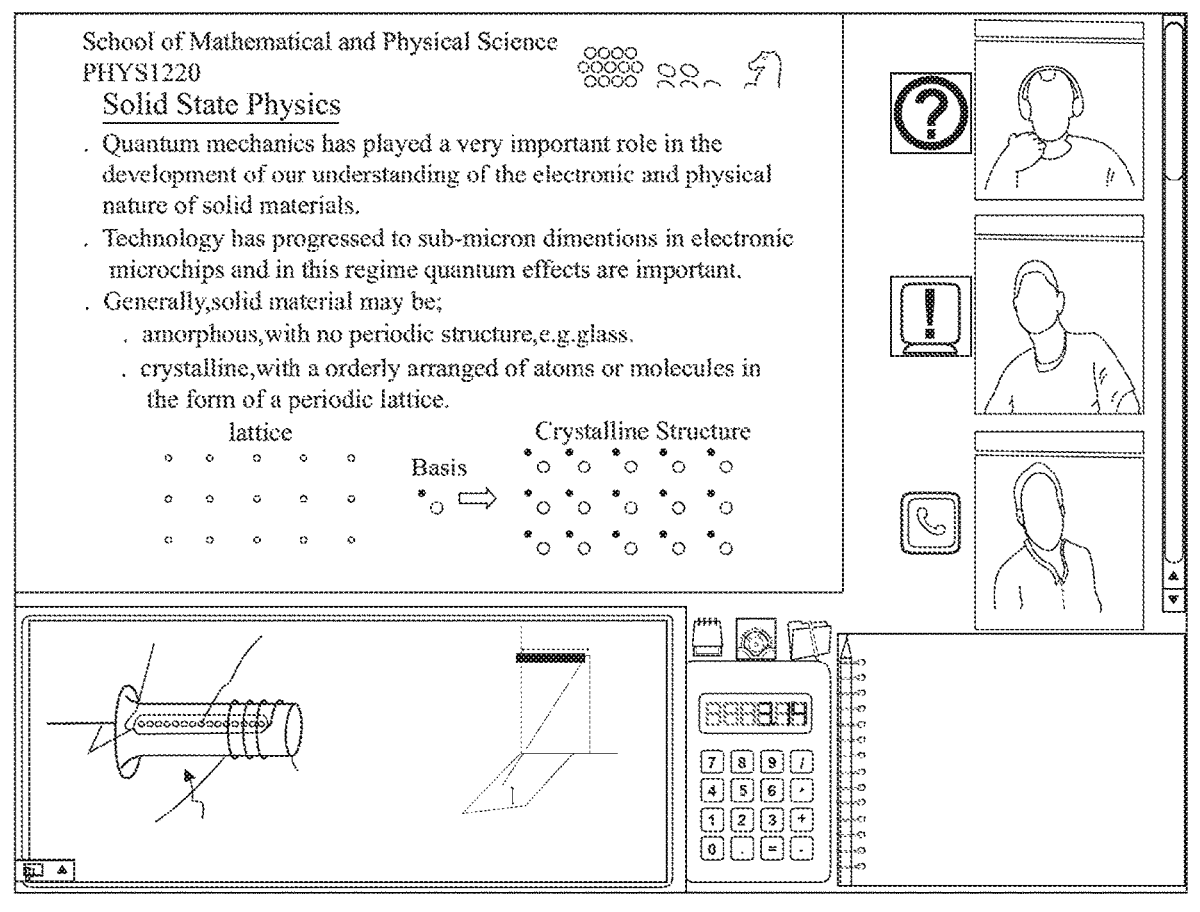

FIG. 6 shows a virtual classroom with e material used as learning medium, based on study of eye movement, pupillary dilation and facial study. The material will be constantly modified and since all peers will be present constant discussion will also be taking place.

If it is observed that the user wasn't taking in the course then pop up questions will be presented on the work area, to check the users understanding hence allow for optimised learning.

Also, based on eye movement, pupillary dilation and facial study of other peers, the student can detect the amount of difficulty or ease his/her peers is having with the class and the problems. Areas that seem to be confusing for the student will be noted down and at the end of each study session these areas will be reviewed.

SWAP Projects

Figure 7:
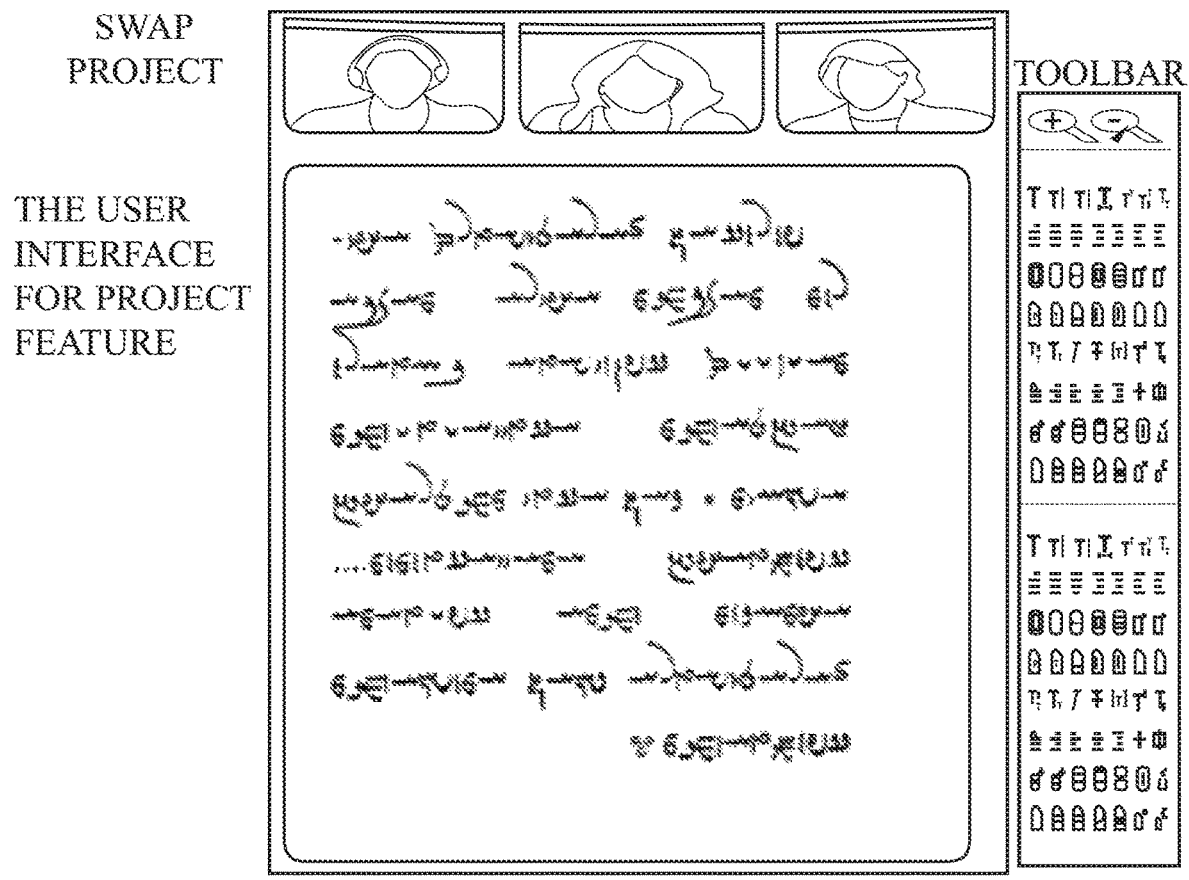
FIG. 7 shows an embodiment of a user interface.

FIG. 7 shows an embodiment of a user interface. For example, another feature that will be present along with the education globe is a single sheet that can be shared across an entire group. All members of the group can make modifications to the sheet simultaneously. All editing and word processing features will be made available. This will allow for rapid completion of project with different parts (e.g. one person may be drawing up some part while others may be writing) being done by different people. In FIG. 7, for example, Linda, Jenny, and Robert can all see each other's' videos. The "Toolbar" includes all possible software devices (e.g., tables, different languages, presentation tools, graphical tools, etc.) In this image, one of the users is able to see what he/she has entered into the project.

Since all progress being made is constantly visible to all the users working on it, a seamless integration will be possible. In fact different people can comment and suggest changes to some or more parts being done by someone else. Constant discussion and visibility amongst the different team members will also be facilitated through audio and videoconference, which will run in parallel with the SWAP Project feature. This will have huge utility in corporate sector, which generally have members working on single project scattered all over the globe.

Figure 8:
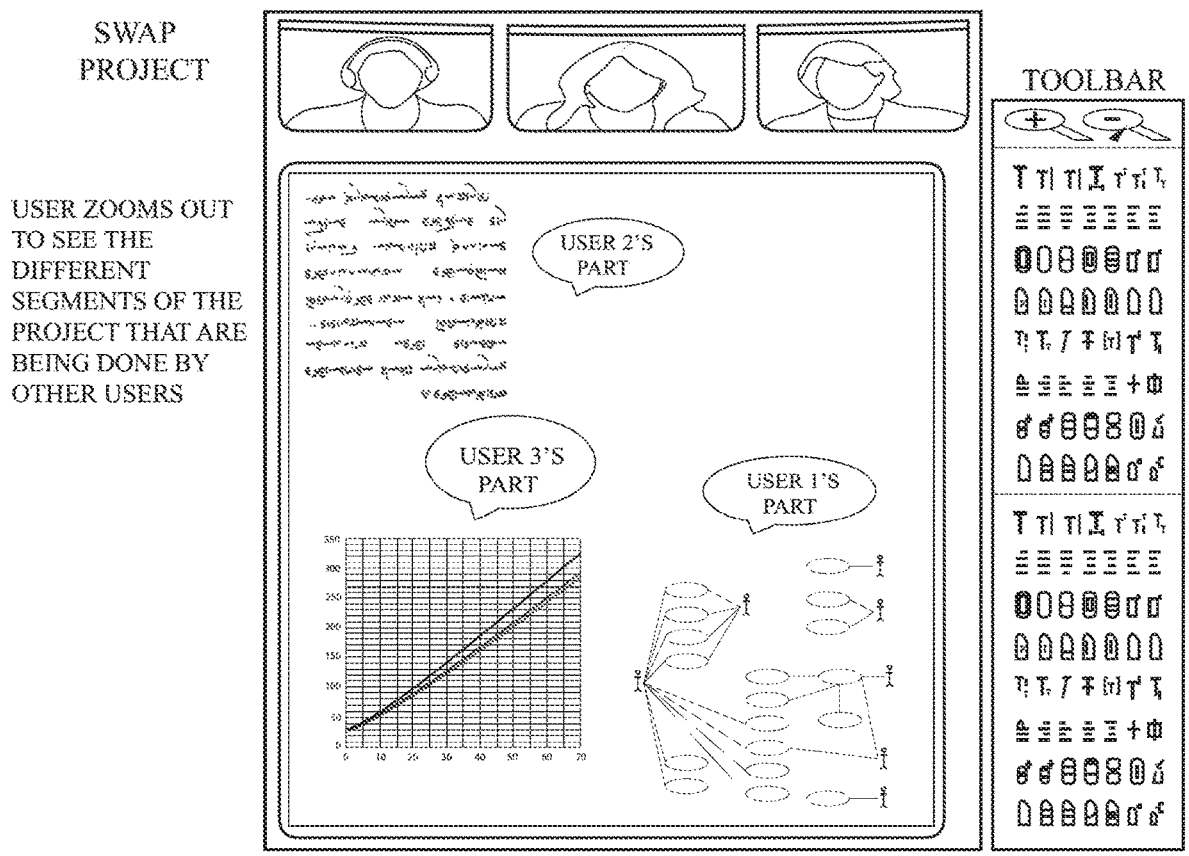
FIG. 8 shows an embodiment of a collated version of the user interface.

FIG. 8 shows an embodiment of a collated version of the user interface. On a single screen, smaller images of various different types of software applications can be presented. Also each user's specific part is labelled automatically with their name. Thus, users are able to see the different segments of the project that are being completed by other users.

Targeted Advertisements

Advertisement will be presented to users based on a. Keyword matching
b. Based on knowledge of user's real-time emotional state.
c. Geographic location and movement pattern (for people using mobile access medium like cell phones or tablets)

The advertisements that will be presented will be guided based on the content of the conversation, the mood of the user and the feature that of SWAP that is being used.

For example people who show high level of cognitive stress may be suggested stress-relaxing medicine, names of specialists and people. People showing emotional extremes like extreme depression may be suggested holiday destinations and retreats, or books.

For mobile users the geographical location, path and movement pattern of the user will be taken into account to provide location based targeted advertisement where product that might appeal to user (predicted by taking into factors like nature of conversation, or media being observed, mood of the user and geographical position). This will enable advertisement agencies to provide extremely specific advertisement.

Healthcare (Remote Diagnosis)

Advanced application can be developed which will collect data generated from cell phones and transfer these to service provider who will analyse the data and transfer it to the healthcare agencies who can then provide diagnosis on basis of the data provided.

Advancement in cloud computing enables us to utilise same apps from different computing devices like tablets, computers, laptops and cell phones. The apps thus developed will not device or platform specific but will only be user specific, they will have an inventory of data mining mechanisms and depending on the device being used select mechanisms will be used.

Figure 9:
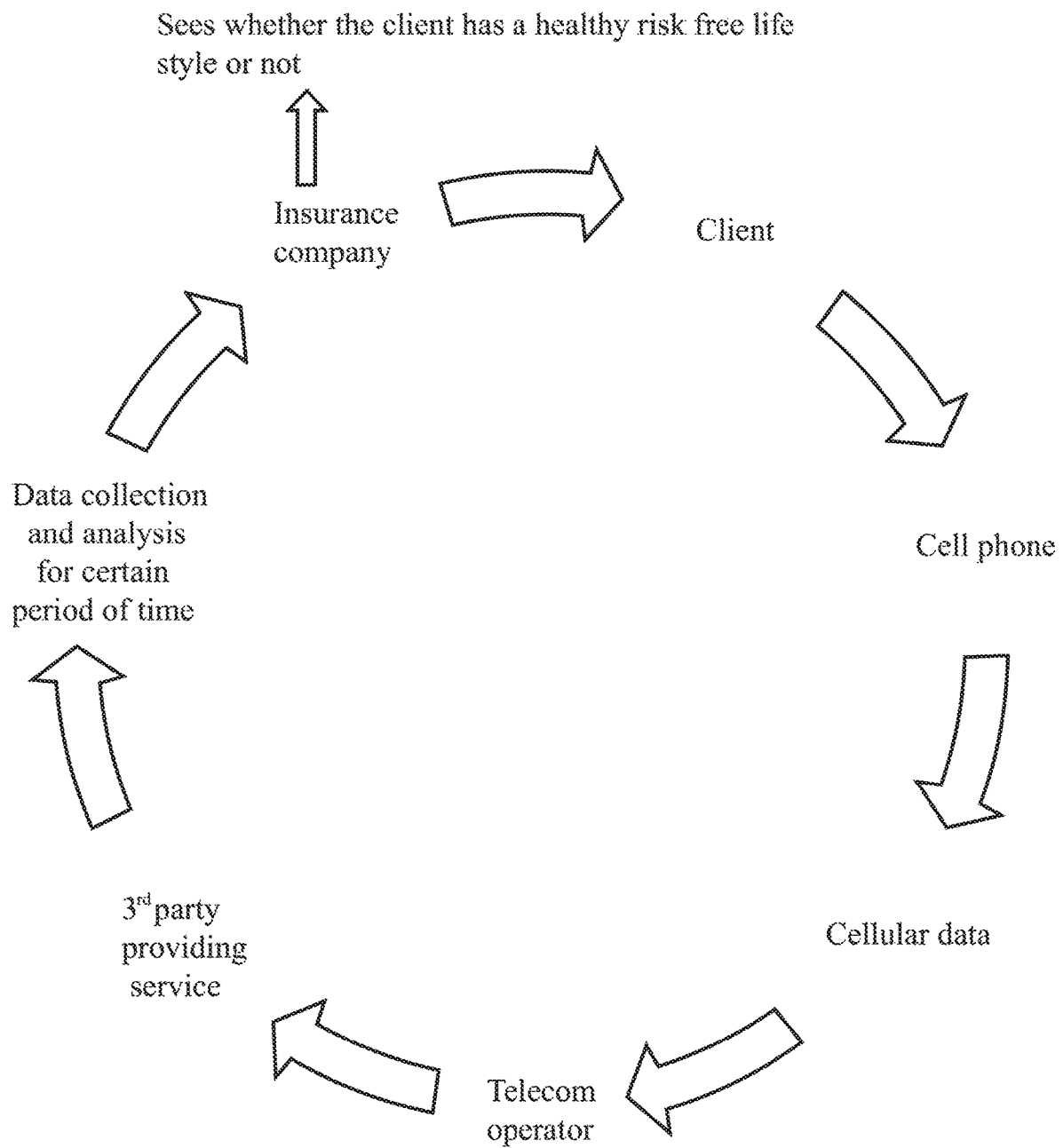
FIG. 9 shows an embodiment of how insurance or health care companies will acquire date through the cell phone of a client.

Combination of data collected from the multiple sources will used to determine lifestyle of the person and this can be used by healthcare and insurance industries. This cycle is depicted in FIG. 9, which shows an embodiment of how insurance or health care companies will acquire date through the cell phone of a client. The cellular data will go through a telecom operator, through a $3^{rd}$ party service provider, who will collect and analyze the data and return it back to the company.

3rd party provider can collect this data only after approval from the individual who owns the cellular device over a set period of time. The data can be used by the individual for personal usage or along with his/her doctor for health analysis. For example, an individual who is fighting with obesity can have his/her cellular data tracked for one month. After analysis of this data, the doctor and patient (e.g., an obese individual) can work together to target some of the problems that the patient. On the other hand, health insurance companies can use this data after approval from the potential customer to determine how healthily he/she is living. If the behavioural choices, emotions, and other everyday actions of the customer seem to promote healthy lifestyle, the insurance company can give discounted rates to such a customer. There are three methods by which current day smart phones can determine the lifestyle, behaviour, or emotions of a person. Time and location, the audio vector of the cellular device, and typing characteristics can be used to analyse a person's health. This data will be collected over a span of time.

Lifestyle data will include:
1. Location information
2. Driving information and movement information
3. His affective state and average cognitive state
4. Habitual information—diet, drinking, etc.
5. Real-time information about physical health The span of time and monitoring parameters will be determined jointly by user and concerned agency.

1. Location Information:

The geographical location of a person can give a general idea of the person's life style and personality. Information like movement over different non-urban terrain is indicative of an adventurous lifestyle. Also information like the places the person visits will highlight many of the persons traits e.g., location data showing that one visits McDonald's everyday indicates that the individual does not have a healthy lifestyle, compared to an individual who visits the gym on a daily basis. After large enough samples of data are collected, a movement map of the individual can be created that shows frequencies of visits to certain locations within a certain range. Using a pattern identification algorithm, doctors or life insurance agencies can more easily analyse location data of an individual and correlate this to his/her lifestyle.

2. Driving Information and Movement Information:

Velocity and acceleration analysis can be done by the GPS on the phone to determine whether or not the individual is a rash driver. Information about speed limits on a majority of roads is present on the maps that are on smart phones. It can be understood that an individual is driving if they are on a road that is traversed upon by vehicles. Usually, GPS tracking provides an accuracy of within 50 meters. So, the speed of a person can be determined by dividing each 50-meter path covered by the time required by the individual to traverse that distance. It will be noted that a person is walking, not driving, on such a road if the speed is significantly below that of the speed limit (like below 10 km/s) for an extended period of time. Even this information is vital, as it informs that the individual is walking on a road that is meant for vehicles, which in itself is an unsafe behaviour. This behaviour will not be confused with cars that are just stuck in traffic, because traffic patterns are now being updated constantly to smart phones, and data about the location and time of the traffic can easily be collected. After confirming that the individual is driving on the road, one can compare the speed of his/her vehicle with the speed to determine whether or not the person is speeding. Even if the individual whose data is being taken down is not the driver, it is important to know if the individual is at risk by being in the same vehicle as a person who is speeding. In addition, if the average velocities recorded in each 50-meter block are fluctuating highly, and the time taken to cover one 50-meter stretch is significantly different than the time taken to cover another, one can see that the driving is "stopping and going" too frequently. An accumulation of data about velocity can easily be translated into acceleration analysis, where the rashness of the driver with sudden accelerations can be determined.

3. The affective and Cognitive State:

The user emotional and cognitive data will be obtained from all communications taking place in form texting, video chat and audio chat from devices like smart phones, tablets computers or laptops. Since the functioning of various features of SWAP like profile+ and virtual classrooms is heavily of dependent on user emotion and cognitive state the apps can gather data from these features to observe emotional and cognitive states of the user during the period of observation. These data can be combined with location data (considering the fact that the user is constantly carrying his smart phone) to affect map of the person. The affect map will show which emotions and mental state correspond to specific locations of the individual.

4. Habitual Information:

Various apps and detection mechanisms can be utilised to determine various habits of the user like eating habits, drinking habit, smoking habit, etc. Apps like Mealsnap, etc. can be detected by the advanced apps of SWAP and used to detect traits of the user.

5. Physical Health Information:

Smart phones have pedometers installed in them and also have the capacity to find a person's pulse. All these features can be used by advanced SWAP apps to give a person's physical health status which can be further combined with time and location information supplement the above-mentioned data.

From this network, an emotional map can also be constructed that shows which emotions correspond to specific locations of the individual. This location tracking combined with the audio vector and typing analysis can indicate which locations the individual should continue going to boost happiness and which locations should be avoided, as they may be correlated to stress, anger, sorrow, etc.

Emotion Analysis

The large amount of data that will be passing through SWAP will be analysed in following ways:

1. Video Analysis
2. Speech Analysis
3. Typing analysis

Figure 10:
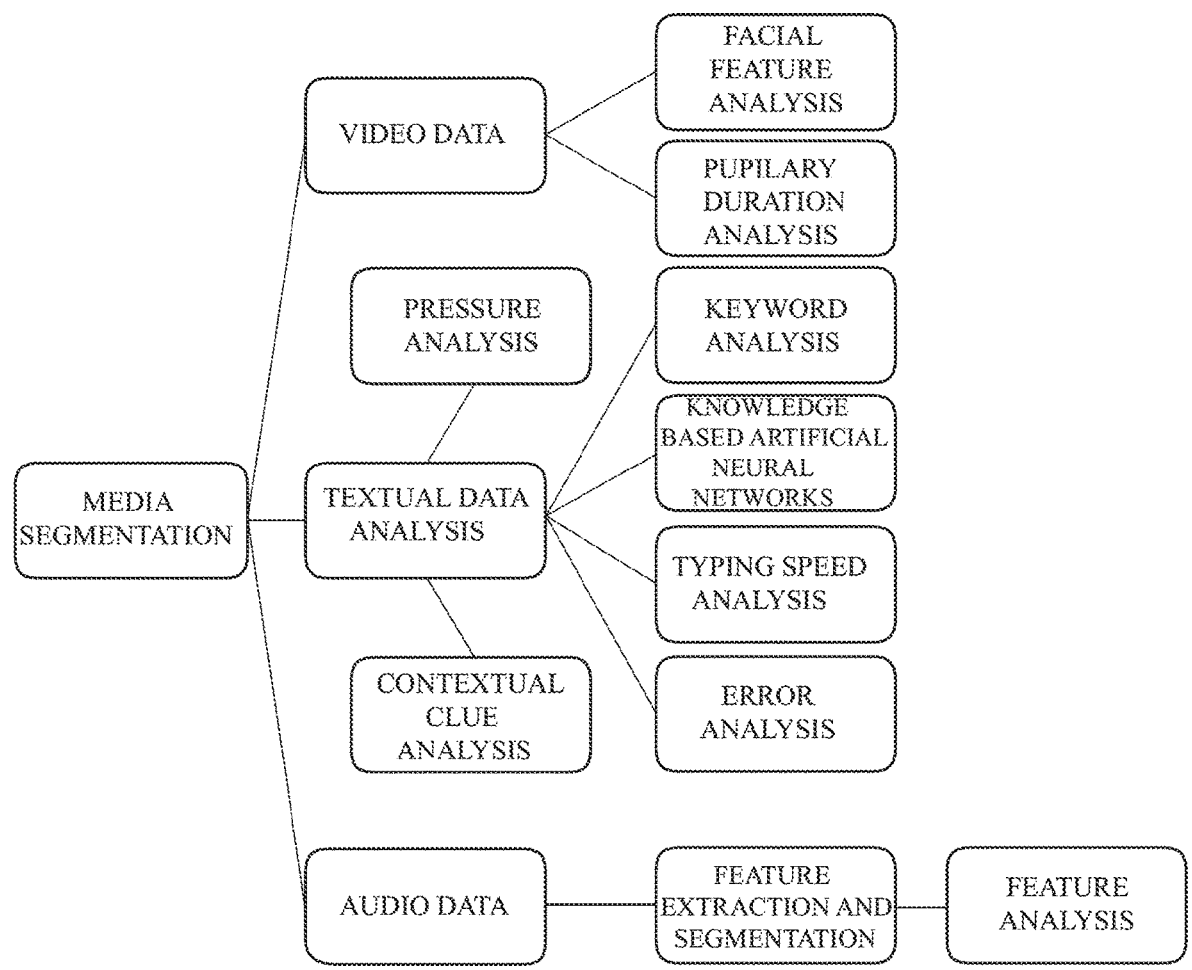
FIG. 10 shows an embodiment of how the media acquired by SWAP is going to be analyzed.

FIG. 10 illustrates an embodiment of how the media acquired by SWAP is going to be analyzed. The data can be organized into three segments: Video, Text, and Audio. Pupillary dilation analysis and facial feature analysis can be taken from the video data analysis. From textual data, keywords, knowledge-based artificial neural networks, typing speed, pressure, contextual clue and error analyses can be done. From audio data, features can be extracted and analyzed. These can be used to determine emotion.

Video Analysis a. Facial Emotion Recognition

The emotion of user is recognized by tracking the movements of some fixed points of the face like the corners of eyes, mouth boundary, etc. The amount of movement of these points in various frames of the video are constantly monitored and the data thus generated is fed in various classifiers like Bayesian Networks, Decision Trees etc. from which we find the emotion of the user.

b. Pupillary Dilation

Dilation of pupils is common phenomena. The causes for dilation of pupils are:

1. Mental stress (cognitive load).
2. Emotion
3. Light stimulus

Our pupils tend to dilate in different emotional situation. Studies conducted have shown that with increase in arousal level the diameter of out pupils increase. Also valance causes our pupils to dilate. But the amount of dilation caused for positive and negative emotion has been found out to be the same. This issue may be resolved with further study in this area—analyzing the rate of dilation and dilation period and also the amount and rate of dilation under combination of different stimuli. Also, while measuring pupil dilation, the dilation caused due other stimuli like light have 2 either ignored or factored out (more study is required in this area). Pupillary dilation is a complete involuntary reflex and hence there no change for us to consciously control it. (This is possible in case facial emotion recognition.) Hence no emotion faking is possible. A distinct difference is apparent for male and female users. So gender classification can be done easily through study of pupil dilation pattern.

2. Speech Analysis

To find out emotion from speech the basic idea is to study the way the voice box functions while producing speech under different emotional states. Depending upon how it functions variations in wave form appear. By extracting the various features of the waveform from which these variations can be detected and putting these (certain combinations of features) into various soft computing models the emotion can be predicted.

Data extracted from an audio vector can be used to determine one's emotional state. The volume and pitch of the speaker can be found without actually recording what the speaker is saying, avoiding any invasion of privacy. The content of the conversation is immaterial to the $3^{rd}$ parties, since only the tonal nature (loudness and frequency) of the individual is being analyzed.

To find emotion from speech first we extract various components of speech, which carry data with respect to emotion. These components are energy, pitch, cross sectional area of vocal tract tube, formant, speech rate and spectrum features and spectral features like linear prediction coefficients (LPC), linear prediction cepstrum coefficients (LPCC), Mel frequency cepstrum coefficients (MFCCs) and its first derivative and log-frequency power coefficients (LFPCs). All these components are extracted from the original speech waveform using various mathematical and statistical techniques. The features can be extracted utilizing various combinations of the features. These acoustic features are used to find out emotions through various classifiers.

Methods that classify emotions from prosody contours are neural networks, multi-channel hidden Markov model, mixture of hidden Markov models these give prediction from the temporal information of speech Methods which classify emotions from statics of prosody contours support vector machines, k-nearest neighbours, Bayes classifiers using pdf (probability distribution functions) generated by Parzen windows, Bayes classifier using one Gaussian pdf, Bayes classifier using mixture of Gaussian pdfs.

Hence from the above-mentioned soft computing techniques we find the emotion of a person. From this his type of collection over a large span of time, general emotional status can be determined via the audio vector.

Data extracted from an audio vector can be used to determine one's emotional state. The volume and pitch of the speaker can be found without actually recording what the speaker is saying, avoiding any invasion of privacy. The content of the conversation is immaterial to the $3^{rd}$ parties, since only the tonal nature (loudness and frequency) of the individual is being analysed.

Typing Analysis

We will utilize the following methods to kind emotion of the user from the text that he types. All the methods will be working in parallel.

1. Finding emotional keywords in textual data and deriving the emotion of the sentence from that.
2. Finding emotion from sentences, lacking emotion key words using Knowledge Based Artificial Neural Networks.
3. By analyzing the typing speed. The various features of typing that we study are time lag between consecutive keystrokes
4. Error level. (Number of times corrections are made in the sentences).

5. Pressure Analysis—the pressure sequence various features extracted like mean, standard deviation, maximum and minimum energy difference, the positive energy center (PEC) and the negative energy center (NEC). PEC and NEC are calculated from mean and standard deviation after normalization).
6. Contextual cue analysis weather, lighting, temperature, humidity, noise level and shaking of the phone The various features of typing that we study are time lag between consecutive keystrokes, number of times back space is used, typing speed and pressure put behind each keystroke, for example, from the pressure sequence various features extracted like mean, standard deviation, maximum and minimum energy difference, the positive energy centre (PEC) and the negative energy centre (NEC). PEC and NEC are calculated from mean and standard deviation after normalisation). Apart from these various contextual cues are also taken into account like weather, lighting, temperature, humidity, noise level and shaking of the phone, and the frequency of certain characters, words, or expressions can be used to determine emotion. The above-mentioned sets of features are fed into various soft computing models (like support vector machines, Artificial neural networks, Bayesian networks, etc), these generate probability towards a particular emotional state individually for each set of features. Also, since in most cases the outcome will be towards the same emotion from computations on each feature set hence fusion methods can be used to compute the over all probability of having that particular emotion by combining the individual results.

Towards Development of a Model For Emotion Detection From Typing Analysis

First, we find out features of typing which is exhibited by most people and features of these patterns which detect emotions. We now develop various soft computing models which allow for the detection of a particular emotion from the typing pattern. To see the efficiency and functionality of these models we conduct sample studies where a software is downloaded by the people whose typing pattern will be analysed. Apart from the typing pattern detection another detection method will also be there to measure the emotional state at the time of typing. These 2 methods will work in parallel and the emotion detected by latter method will be taken as reference and later during analysis it will be seen whether the emotion predicted by the former method matches with the reference.

In the latter method the peoples' emotional valence will be detected by study of their facial muscles which can be done by use of a simple web-cam (generally available with their computer or laptop) and arousal will be detected by measuring the galvanic conductivity of skin measured with wristband with this capability (already a commercial product manufactured by a company called Affectiva).

The above-mentioned method departs away from way experiments have been done on typing analysis recently. In these experiments the candidates whose pattern will be analysed are given the software which analyses the typing pattern but reference emotion is found out through questionnaires that enquire about the emotion of the person before he starts to type.

Again, this will not be a privacy issue because these third parties will not access full texts. They will just automatically search through them for the frequency of specific words or expressions that may correlate to the individual's emotions. These data will not just be collected once, but over a long span of time. As a result, the overall emotional and behavioural state of individual will be determined. So, a person typing very fast on a shaking phone, with high pressure under the keys, and using a high frequency of unpleasant words used in his/her texts can reveal anger or stress. However, if data that points to this behaviour is only collected once or twice in a span of a month, it will not be regarded as very important, as everyone has some infrequent expressions of anger or stress. However, if a majority of typing data is like this, a doctor of insure company can infer that the individual is constantly angry or stressed out, which is not good for health.

Mental Health Tracker

Currently 1 in 4 Americans have a mental disorder. It is becoming increasingly important to identify mental disorders at younger age, when symptoms are still slight. It is thus essential for primary care physicians in addition to psychiatrists to be able to recognize mental disorders.

In an embodiment, the DSM IV-TR (Diagnostic and Statistical Manual for Mental Disorders) and DSM IV-PC (Diagnostic and Statistical Manual for Primary Care) version, which are the manuals used by doctors to determine both the presence and category of mental disorder, could be included in as part of a computerized algorithm to help doctors for patient tracking. The DSM IV-PC (meant for primary care physicians, who are not specialized in mental disorders) has organized symptoms that create a diagnostic algorithm. This manual is concise and fully compatible with the wider used DSM IV-TR, which is used by psychiatrics.

Figure 11:
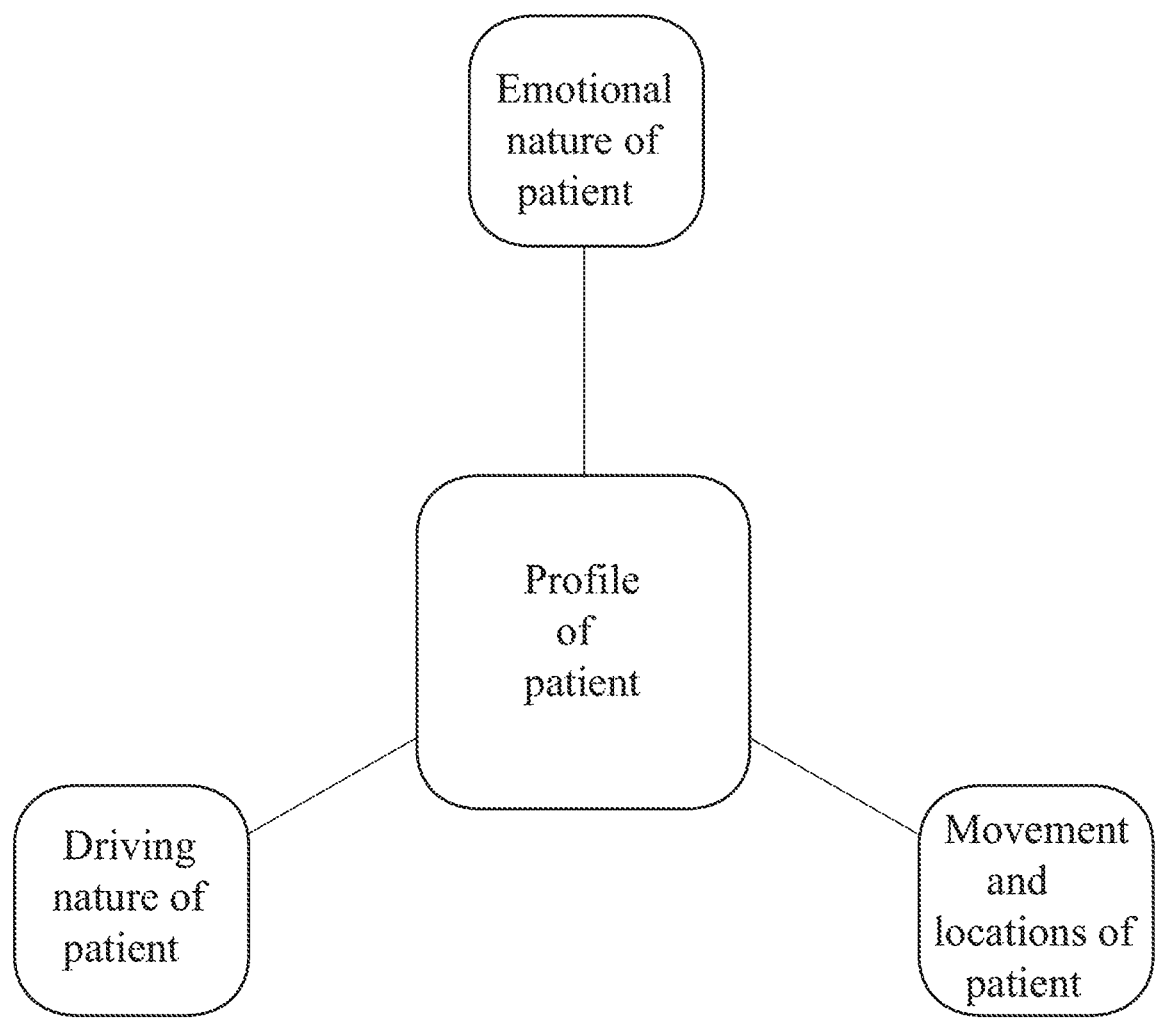
FIG. 11 shows an embodiment of a non-invasive patient tracking method.

Primary care physicians (PCP) have made many initial diagnoses of mental disorders. However, many diagnoses remain undetected, as PCPs generally only have check-ups with patients one or twice a year, and mental disorders, at first may be difficult to observe, as there are no standardized tests for mental disorders. Due to the difficulty in diagnosing a mental disorder within the limited face-to-face patient-doctor interaction, it can be extremely helpful for doctors to use a non-invasive patient tracking method of an embodiment as shown in FIG. 11, which shows the main aspects of SWAP that can be used to create a profile of the patient that can then be analyzed by the algorithm of the DSM-IV and by doctors.

Figure 12:
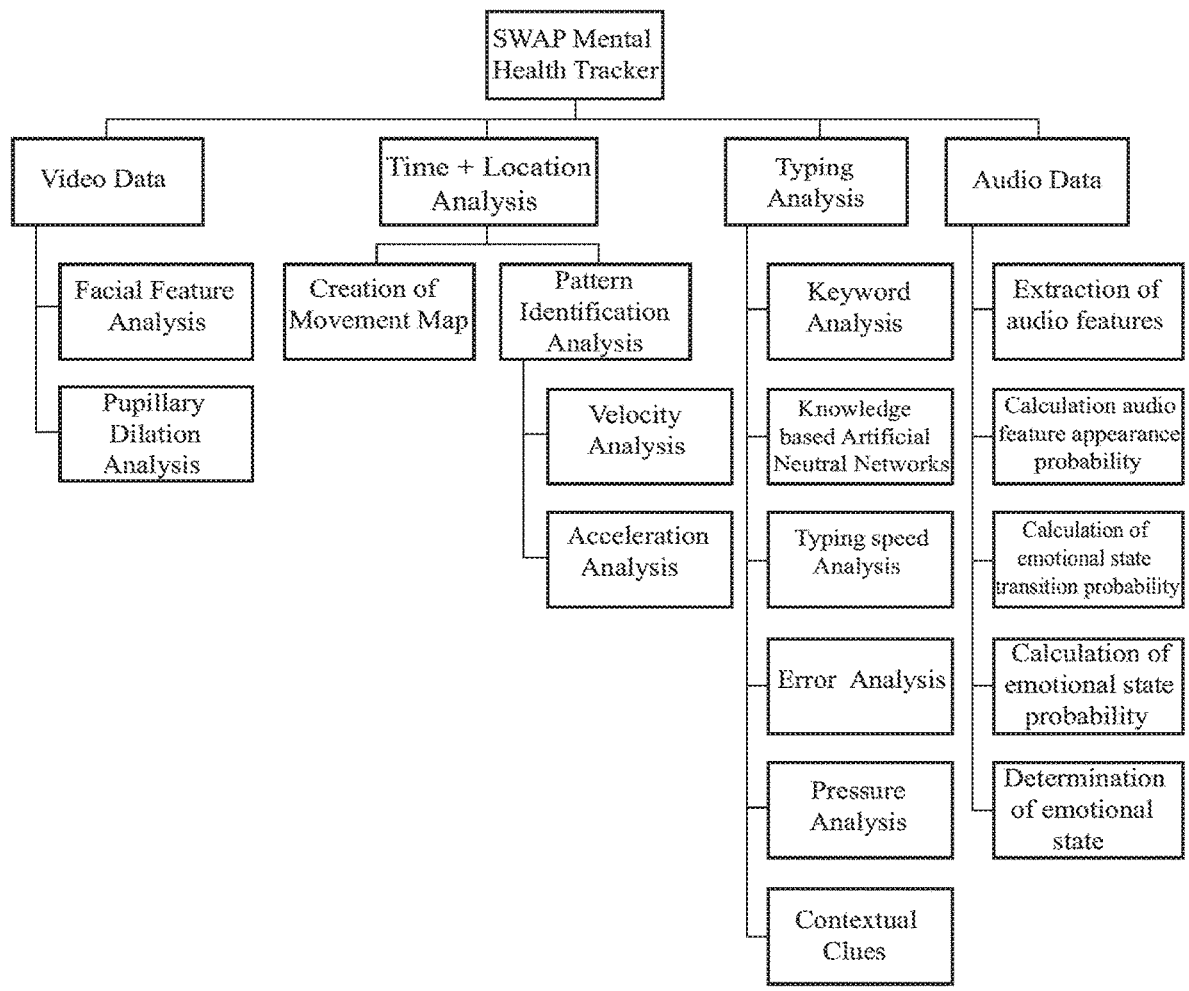
FIG. 12 shows a flow diagram that delineates possible tracking mechanisms.

Doctors can track their patients using methods detailed in other examples of our patent. FIG. 12 shows a flow diagram that delineates possible tracking mechanisms. FIG. 12 shows that the proposed tracker can use video data, time and location analysis, typing analysis, and audio data in order to understand the patient's emotional state. Over a week or month long analysis, this tracker will then use an algorithm from the DSM-IV in order to identify an initial mental diagnosis. With the use of the guidelines in the DSM-IV-PC, the algorithms created by the manual can be used along with our tracking system to provide a primary initial screening for patients for detection and type of mental disorder. Thus, SWAP's Mental Health Tracker can help a physician better understand his patient's needs.

An embodiment relates to a method of establishing a collaborative platform comprising performing a collaborative interactive session for a plurality of members, and analysing affect and cognitive features of some or all of the plurality of members.

An embodiment could include some or all of the plurality of members from different human interaction platforms interact via the collaborative platform.

An embodiment could include displaying of targeted advertisements or notifications based on the context of the interactive collaborative session.

An embodiment could include measuring effectiveness of the displaying of targeted advertisements or notifications.

An embodiment could include integrating an application or a device within the collaborative interactive session.

An embodiment relates to a computer implemented system comprising: a storage medium configured to store a collaborative interactive session data; and a processor configured to perform a collaborative interactive session for a plurality of members, wherein the system analyses affect and cognitive features of some or all of the plurality of members.

An embodiment could include some or all of the plurality of members from different human interaction platforms interact via the collaborative interactive session, wherein the different human interactions platforms comprise social media platforms.

An embodiment could include the system being further configured to display targeted advertisements or notifications based on the context of the interactive collaborative sessions.

An embodiment could include the system being further configured to measure effectiveness of the displaying of targeted advertisements or notifications.

An embodiment could include the system being further configured to integrate an application or a device within the collaborative interactive session.

An embodiment could include a sound and/or video hub, wherein the sound and/or video hub allows any member of the plurality of the members to play a song and/or a video and simultaneously allows some or all of the plurality of members to listen and/or watch the song and/or the video played.

An embodiment could include audio and/or video synopsis of the collaborative interactive session for the plurality of members using a sound and image-processing technology that creates a summary of an original full-length audio and/or video.

An embodiment could include the system being configured to determine a mental health of a patient by analyzing one or more of audio, video, textual and location data of the patient, and evaluating the data in a standardized model.

An embodiment relates to a tangible non-transitory computer readable medium comprising computer executable instructions executable by one or more processors for establishing a collaborative platform comprising performing a collaborative interactive session for a plurality of members, and analyzing affect and cognitive features of some or all of the plurality of members.

An embodiment could include some or all of the plurality of members interact from different human interaction platforms.

An embodiment could include computer executable instructions executable by one or more processors for displaying of targeted advertisements or notifications based on the context of the interactive collaborative sessions.

An embodiment could include the executable instructions comprising instruction for determining a mental health of a patient by analyzing one or more of audio, video, textual and location data of the patient, and evaluating the data in a standardized model.

SWAP and Remotely Providing Healthcare

The SWAP platform is useful in multiple aspects of healthcare for both patients and physicians. The ability for the SWAP interface to be easily accessed by doctors and patients throughout the world tremendously improves healthcare delivery. In addition, SWAP has the ability to be seamlessly integrated with many of the existing and upcoming virtual healthcare technologies.

Figure 13:
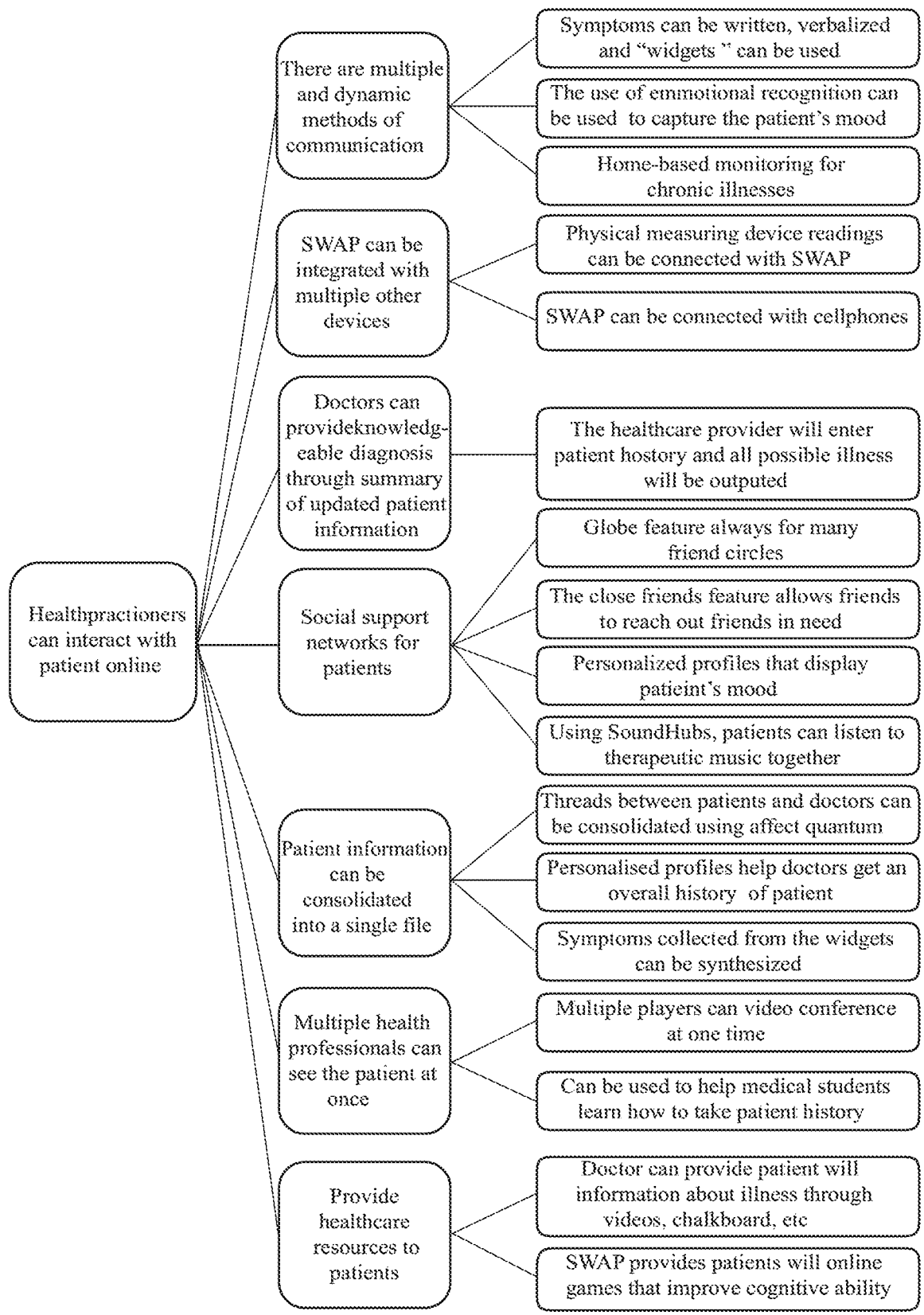
FIG. 13 shows a flow diagram of an overview of SWAP's functionalities in healthcare delivery.

FIG. 13 describes an overview of SWAP's innovation in healthcare delivery. Overall, SWAP provides a dynamic virtual communication platform that, in the context of healthcare, allows for heretofore unparalleled virtual synergies in the complex web of interactions between doctors and patients around the world.

The embodiments of caregiving to a patient include: continuously monitoring and measuring the patient using one or more devices; and allowing a caregiver to have real-time interactions with the patient remotely.

One can include real time alerts for the caregiver and optionally the patient too by not only looking at a single day's data, but optionally by looking at long term data and optionally comparing long term and/or short-term data against models of health vitals. Furthermore, holistic analysis of data can be done by combining short term health data with long term health data along with the patient profile. Long term health data can include health data obtained over a period over a month. Short term health data can include health data obtained over a period of a day, an hour, or ten or less minutes. If needed, the caregiver can interact with the patient remotely as and when a situation arises requiring remote interaction. Such a situation may include when a model of health vitals indicates development of an illness, when a deviation of short-term health data from long term health data, and when real-time monitored vitals indicate a life-threatening emergency.

The caregiver can provide treatment remotely. Providing treatment remotely may include sending control signals to adjust doses of medicine given to a patient receiving intravenous medications, providing instructions to the patient, providing instructions to caregivers local to a patient, calling paramedics, etc. The effectiveness of the treatment can be monitored remotely. Monitoring the effectiveness of a treatment may include receiving health data (long term and/or short term) of a patient, receiving report from caregivers local to a patient, receiving signals to an monitor instrument, etc. The treatment can be adjusted remotely based on effectiveness monitored remotely.

Health Care Data Analytics

This tool can be used to diagnose the patient's symptoms using up-to-date knowledge bases. The data may be already in the SWAP repository or may be a standalone knowledge base accessible to SWAP. SWAP may be seamlessly integrated into the online knowledge basis (including publicly available and customized software meant for certain illness, etc). It enables doctors to diagnose the illness of patient is a much quicker way. This is called a federated search.

Diagnosis may include: data collection and storage in the knowledge database; patient symptom keywords generation; and query the knowledge database using the keywords. The keywords may be generated using the data collected from the SWAP platform. The federated search will compile a diagnosis.

Support Groups

SWAP can serve as a social support network for patients. SWAP is also a social media outlet for patients. If a patient chooses to, he or she may join a support group that has a similar disability or illness. These groups will have doctors overseeing conversations and to answer questions. Thus, people can connect with other people who have similar illnesses.

Support group members can exchange their data with the support group. A senior patient could help the newer patients. Patients can make their own profile. SWAP can be used to help connect patient to healthcare practitioner or patients of a similar nature. Doctors can be alerted of dangerous depression related problems: Multiple doctors can work on a single patient's diagnosis simultaneously;

continuous education for the patient. Communication within the support group can be used to update the patients' profiles and become part of the health data of the patients the healthcare practitioner can access and use.

SWAP could use multiple and dynamic methods of communication to interact with and monitor patients. SWAP removes fragmentation within video communication, a vital tool that is applied to patient-doctor interaction as well as patient-patient interactions among related disease groups. Healthcare professionals have the ability to monitor patients' symptoms. Through integration with existing health monitoring technologies, SWAP serves as an interface for the physician to understand the patients' state of being. For example, a plastic surgeon is able to have a consultation via the platform. The surgeon is able to take images of the patient while video chatting, perform pictorial analyses with the drawing tools, and storing high quality measurements into a database.

SWAP enhances home-based monitoring of various chronic conditions. Healthcare professionals can continually monitor their patients' symptoms and overall health, a feature that is useful for diseases such as obesity and diabetes. There are 4 main categories of monitoring—1) Wellness (height, weight, exercise, etc.), 2) Chronic Illness Measurements (BP, glucose, etc.), 3) acute care/rehabilitation 4) aging. Overall, SWAP creates a continuous interaction between chronically ill patients and their physicians.

SWAP's emotion analysis technology can be used to understand patients' mental state while video conferencing. Technologies in the realm of video analysis, speech analysis and typing analysis may be employed. Facial emotion recognition, pupillary dilation, voice box functions, emotional keywords, typing speed analysis, error level, knowledge based artificial neural networks and pressure analysis, amongst others, may be utilized to collect mental and bodily health data to monitor the patient. Various patients' behaviour may be used to extract one or more metrics that characterize the patients' mental state.

Patients unable to express symptoms through traditional video chatting, perhaps due to a language barrier or physical inability, are able to convey symptomatic information through various other interfaces. The blackboard interface allows patients to express their current state in multiple ways. Integration of a translation software has the ability to surpass the language barrier preventing many doctor-patient interactions to flourish.

Figure 14:
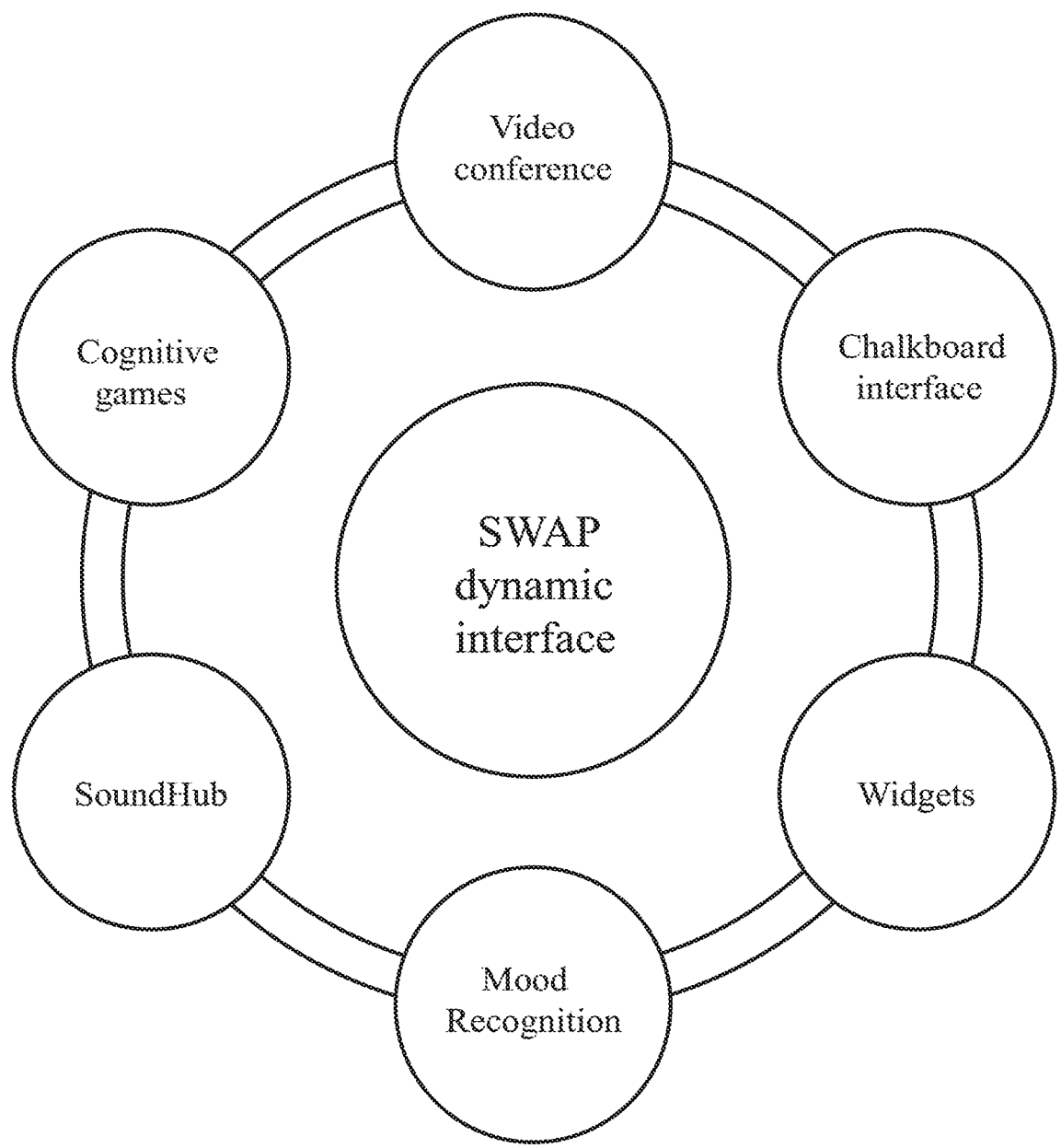
FIG. 14 shows a flow diagram showing SWAP's ability to provide a dynamic collaborative platform.

FIG. 14 describes SWAP's ability to provide a dynamic collaborative platform with features such as chalkboard interface and mood recognition to enhance the traditional video conferencing interface.

SWAP can be integrated with multiple other devices. SWAP uses multiple platforms, thus many of the applications that are already created on smartphones can be integrated into one combined report. Thus patients can use multiple home monitoring applications that will present its data onto the SWAP interface. The SWAP platform may be integrated with physical measuring devices (e.g., blood pressure cuff or glucose meter). The readings may automatically be inputted in the patient's history. For example, a diabetic patient who checks blood glucose level every day using a glucose meter can have his readings automatically inputted into the SWAP patient history section. This can be accomplished through "plug-in" technology similar to a smartphone that can be connected to a computer.

SWAP is not limited in the way it receives data. For example, Internet is an exemplary way for SWAP to receive data. Other ways may include mobile network, satellite, radio, etc. For example, SWAP can be connected to cell phones or other mobile devices. People in rural areas can text their conditions to their SWAP account. A doctor may see these messages and their response may be texted back to their patients. This can really help people who are in low-income areas and are unable to have internet access. Also, people who are traveling can be benefited from such an interactive text service. All texts may be saved onto the SWAP platform to facilitate a consolidated patient history.

An integrated search engine may be included in SWAP and allow for increased doctor's understanding of new scientific discoveries. SWAP integrated with a search engine that encompass up to date medical literature and frontiers in science and medical technology to enhance physicians knowledge of the most accurate diagnoses, current standard of therapy and state of the art therapeutics and treatments while interacting with the patient. It is currently extremely difficult for doctors to accurately recall and remain up to date with new data published about diagnoses and treatment options. The search engine will enable doctor's type the symptoms of the patient and will quickly give an accurate summary and subsequent detailed analyses of all the medical literature currently available that are relevant to the patients' medical conditions. Additionally, the chalkboard interface's academic integration allows a medical professional to use the power of scientific and diagnostic information available on the web to inform their decision.

Figure 15:
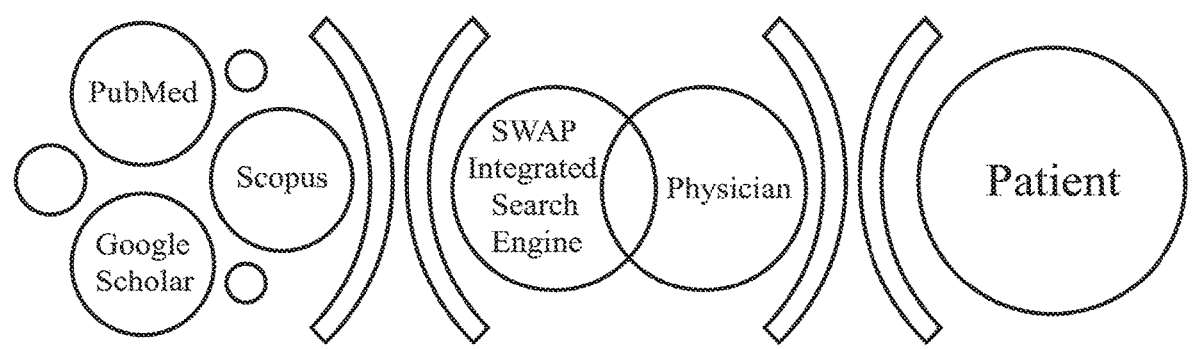
FIG. 15 exemplifies the added benefits of virtual healthcare delivery through SWAP.

FIG. 15 exemplifies the added benefits of virtual healthcare delivery through SWAP. Integration with state-of-the-art medical databases while utilizing the SWAP platform to communicate with patients tremendously enhances access of information for physicians and allows for unparalleled virtual diagnostic capabilities.

SWAP can serve as a social support network for patients. SWAP is also a social media outlet for patients. If a patient chooses to, he/ or she may join a group that has a similar disability or illness. Such groups can also work as discussion forums or message boards where people can hold conversations in form of posted messages. The messages may be at least temporarily archived. The archived messages can serve as a central repository for information about a particular disease and/or condition. Doctors and patients can exchange information about symptoms, diagnoses, treatments, as well as prophylactic measures for particular diseases and/or conditions. Each "thread" is, in general, specific to a condition or disease. Once a patient and/or doctor posts a message to a thread, other patients and/or doctors can see the message and respond accordingly. Such message may be posted anonymously to protect the privacy of the patients.

Alternatively, such groups can work as chat rooms where people can hold conversations in real-time and get suggestions and solutions to relatively more urgent matters. Like the discussion forums, the chat rooms can allow patients and/or doctors to discuss symptoms, diagnoses, treatments and/or prophylactic measures anonymously.

There can be separate and dedicated web-based and/or mobile application interfaces for various aspects of SWAP. For example, there can be a separate application for the discussion forum, another separate application for the chat room, yet another application for monitoring physical and/or emotional data. Alternatively, all the various aspects of SWAP can be integrated into one single interface through which separate applications can be called on as needed. In either case, personal data on SWAP can be protected by a single-step authentication process such as a login and a password or a pattern, or a 2-step authentication process requiring a frequently refreshed pseudo-random numeric, alphabetical, alphanumeric or other phrase required to access the information. Alternatively, biometric authentication such as, for example, iris scan, face-recognition, fingerprint recognition, voice recognition, or any other biologically unique characteristic may be used as a means to protect the data accumulated through SWAP. These groups will have doctors overseeing conversations and to answer questions. Thus, people can connect with other people who have similar illnesses.

This application will be SWAP may organized interactions into several spheres known as "globes". Each globe will provide a base interaction for multiple users to collaborate. SWAP's interface may be customizable to the user's preference. Based on his or her interests, involvements or activities, the user may be able to select the globes, and the platforms of interaction therein that pertain to themselves and add the selected globes to his or her own personalized interface. SWAP may allow users to create and publish their own globes for private or public use. For example, the social networking platform can use SWAP's sound hub feature. Doctors or other social networks friends can play therapeutic music that all those included can hear. Listening to music together makes it a social experience and thus increases its therapeutic value. Also, the music can be reached across the world simultaneously.

SWAP may include an arcade feature that allows patients with psychological disorders to play medical games, or for geriatric patients to benefit from cognitive and memory building exercises. Through SWAP, patients can interactively participate with each other.

The way most social networking sites function, they mainly act as a great platform for data storage, sharing and communication. But they these are all a far cry from true social interaction simulation. In other words, in no way are these anywhere near how we interact in society. Thus the profiles of SWAP will be a system which will be much closer to how we remember people, conversations and moreover how we forget. The large amount of data that get passed through the SWAP platform will be analyzed and this data will be used to shape the SWAP profiles. The way other people's SWAP profiles will appear to us will be similar to how we remember people in reality. In this area we try to mimic the way in which we remember people. The profile's emotion feel will be the general emotion that we generally exhibit when we communicate that with that person through any form of media (video, text or speech) (obtained from analyzed data from conversations taking place). Keeping in trend with how we remember people in reality, since how a person is seen by is strongly shaped with event and experiences we share with that person. The profile of the person will bear events, having strong emotions behind them. Any sort media—like text, speech, video or pictures. Texts can be presented simply as they are, videos will we presented like snapshots with the option to be played by the user. The profile of SWAP will be dynamic in nature constantly changing reflecting the mental state of the user. The real-time mental state will be determined from the various analysis methods, which will be applied on the data passing through SWAP. Under a state of extreme emotion such as depression the user profile will be able to reflect this state. This will allow for other people to be notified of the user's emotional state and hence help him get back normalcy through communication. Through analysis 'close friends' can also be identified who under the above-mentioned situation will be notified.

The analysis of data through SWAP will allow the application to identify people with whom the user has discussions of high emotional content. A database of sorts can be created which will store people with whom the user has discussion of high emotional content such as high positive emotion content, high negative emotion content, people with whom through communication emotion changes from negative to positive. Also, people with whom there isn't communication of high emotion content but volume and frequency of communication is very high, these people will also be identified as 'close friends'. Whenever the user is in a state of emotional extreme then the user's profile will be highlighted in the homepages of the 'close friends'.

Multiple health professionals can see a patient simultaneously. The SWAP interaction model facilitates online interactive communication for multiple players necessary for remote healthcare delivery. For example, primary care physicians, nurses, speciality physicians and the patient could all dynamically interact to arrive at the correct diagnosis.

SWAP allows multiple physicians around the world to collaborate and come to a diagnosis on a patient, as it serves as a great interface to share information such as patient history, scientific insight and medical expertise. A doctor can transfer patient information to doctors who can best understand the patient's needs. This is both in terms of medical speciality and culture (including language).

For students who have conditions, doctors can directly present the school nurses with the relevant medical information of students. Also, for students with learning disabilities etc. teachers can send information to the doctors regarding the student's learning progress. SWAP is also an excellent platform for insured patients who are travelling. They can still regularly see their personal physician via the internet.

SWAP allows for medical professionals to disseminate information to multiple parties simultaneously in the interactive platform. For example, a surgeon in Washington, D.C. is able to display a video of a specific procedure to multiple colleagues around the world while video conferencing and using the chalkboard interface to take notes. SWAP can be used for medical education, as it serves as the perfect interface for medical students to watch live videos amongst other students and take group notes, etc. The platform will protect all HIPAA laws when transferring such information to students. SWAP can be used by residents and doctors as an evaluation technique.

Figure 16:
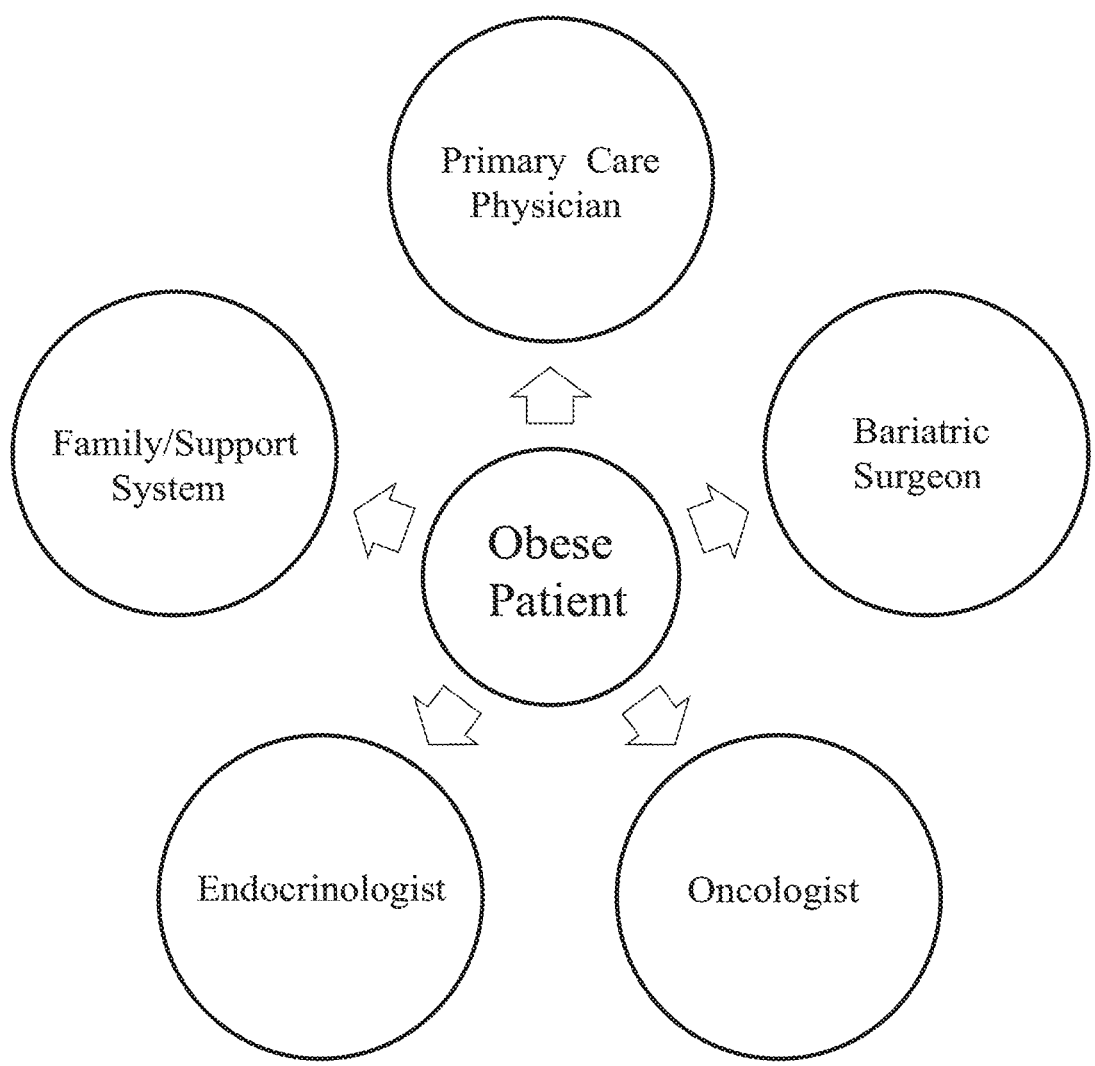
FIG. 16 shows a flow diagram showing the ability of SWAP healthcare delivery to form collaborations in treating a patient.

FIG. 16 describes the ability of SWAP healthcare delivery to form collaborations in treating a patient. Here, an obese patient that is likely to have complications in various therapeutic areas is able to be simultaneously explored by multiple physicians from around the world, along with his close family and support system provided by SWAP social networks.

SWAP can consolidate patient information and history. Conversations between doctors and patients can be summarized using the chatting thread with affect quantum. The basic flaw which makes social interactions unrealistic is that every bit of data is remembered which not case in real day-to-day life interactions is. To replicate these communications that will be happening through SWAP will follow a similar pattern. The comments of the thread will slow start to deteriorate i.e. fade away. The period after which the part of the thread is completely forgotten will be a sort of threshold time, which will be close to average human being time for memory retaining. Memories having high cognitive strain or emotion attached will have much higher threshold time. In other words, each quantum of media will have Affect quantum attached to it.

Additionally, patient information gained from symptoms that described through widgets, verbal and written communication are consolidated in the patient history using the affect quantum method described above.

Also, all information gained from external devices (e.g., glucometer) is stored and captured into a graph so that patient information is neatly tracked and displayed in a easy to read manner. All texting conversations are also recorded and major conversations are highlighted using the affect quantum method. Lastly, the patient's personalized profile serves as an overview for of the patient's basic information, close friends, and mood.

Figure 17:
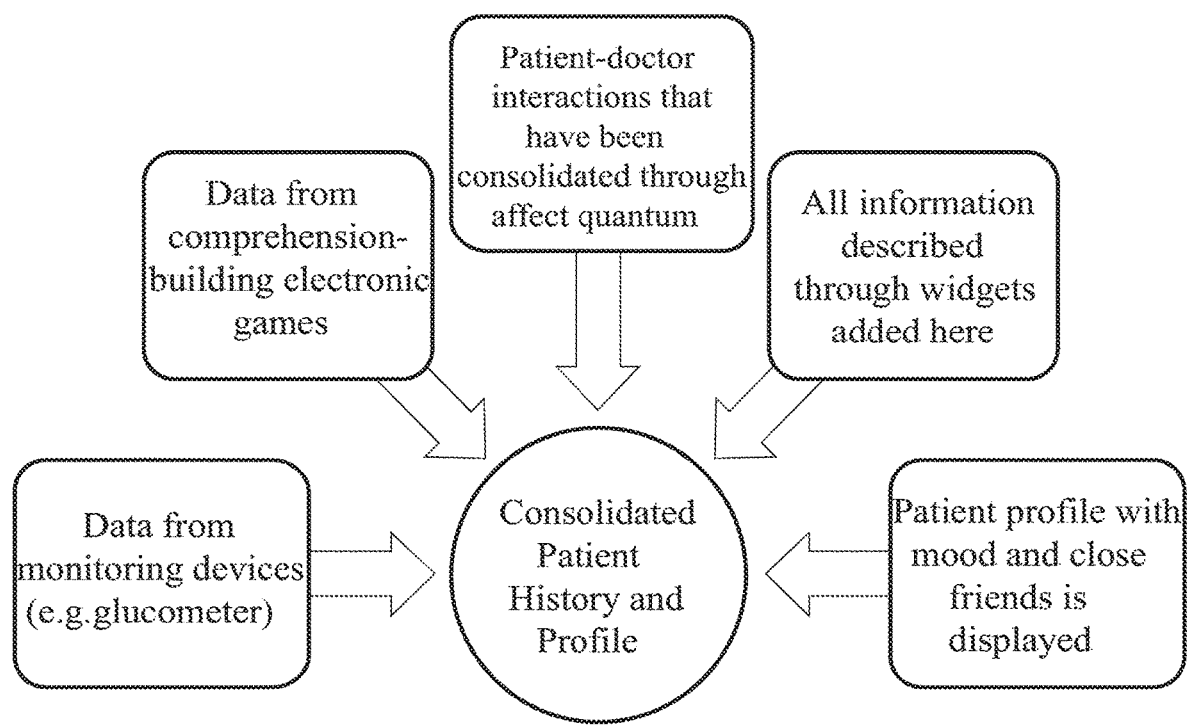
FIG. 17 shows a flow diagram showing SWAP's ability to collect critical data from patient interaction and consolidate into a patient's profile for subsequent analyses

FIG. 17 describes SWAP's ability to collect critical data from patient interaction and consolidate into a patient's profile for subsequent analyses.

SWAP can provide educational health care resources to patients. SWAP allows physicians to explain conditions to patients via interactive interfaces, such as video, blackboard interface and eLearning technology. This is especially helpful for children, in which cases it is often difficult for them to understand their conditions. SWAP harnesses the capabilities of mobile and tablet technology as well as its touch screen technology to allow users to interact with the chalkboard through a much more seamless and natural medium. Furthering this concept of seamless, our product will incorporate handwriting recognition software that will be able to decipher and identify what the user is writing based on the domain selected and the context of the information already present, to convert the users' handwriting into digital text that will appear much more legible and clear to all the users. The various features integrated throughout the SWAP platform allows for continuous patient education even when the healthcare professional is absent. For example, interactive exercise modules for overweight children could serve as tools in the prevention of childhood obesity.

Figure 18:
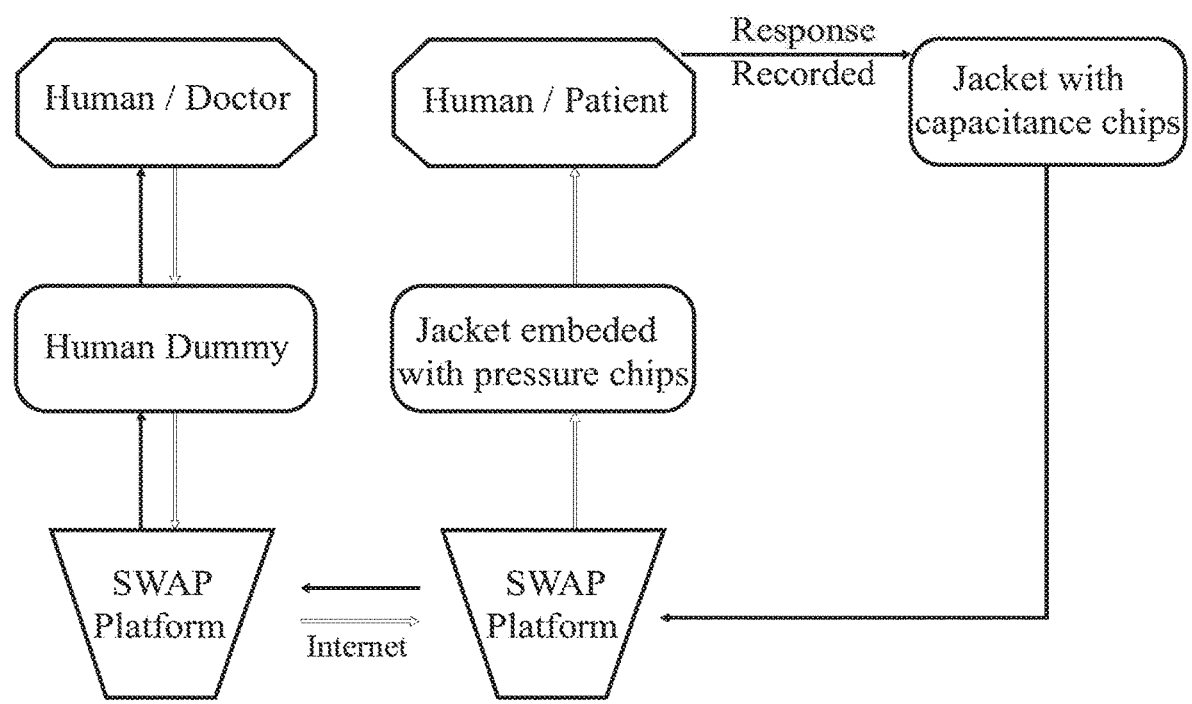
FIG. 18 shows a flow diagram for transmission of two way touch sensation.

SWAP can be used as a system that allows humans to send touch remotely to other humans for medical diagnostic purposes. FIG. 18 shows a flow chart for transmission of two way touch sensation between two people, for example, a doctor and a patient. This system allows for tactile interfacing while utilizing the visual and auditory channels of communication through the SWAP platform to develop a comprehensive method of medical examination to further the current state of remote medicine. The receiver or the patient will wear a jacket embedded with touch sensitive chips that can stimulate a particular area of skin to create the sensation of touch. The sender or doctor will use a medical doll to pinpoint specific areas of contact. By touching a certain area on the doll, a computer will convert that information and send it through the Internet, which the jacket will then receive, translating it into an electrical impulse that models the physical sensation of touch.

The current capabilities of remote medicine are limited to simple communication between physicians and patients but have not been expanded to truly simulate the physical aspects of a medical examination. The implementation of virtual touch presents a solution to this void in the industry, allowing doctors to completely characterize a patient's physical state.

Figure 19:
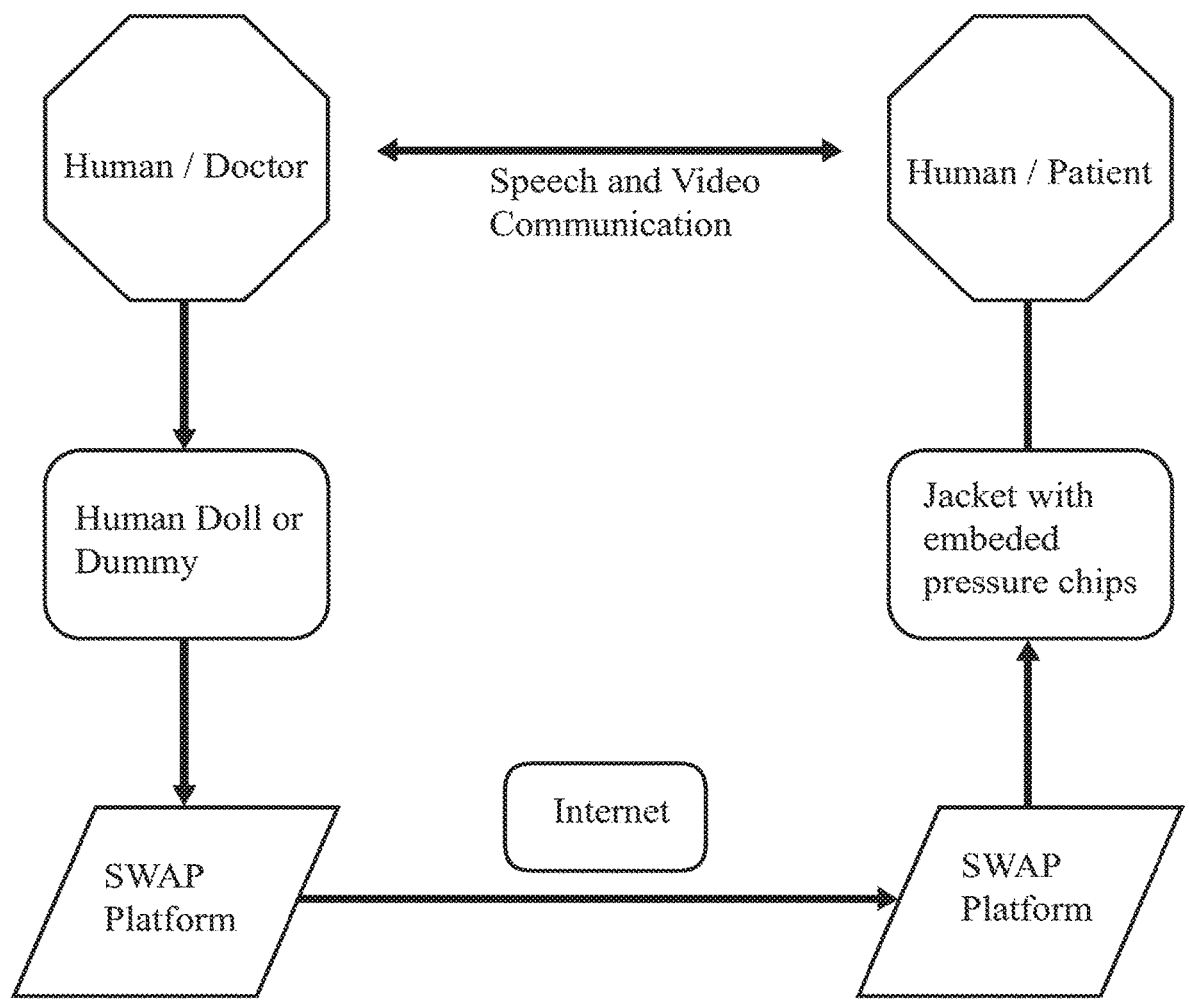
FIG. 19 shows a flow diagram for transmission of one way touch sensation.

In one embodiment, SWAP can be used to create a one-way channel of touch communication as shown in FIG. 19. For example, if a doctor hopes to assess where a patient's pain lies, the doctor can touch specific areas of the human doll, listening to the patient's response to determine which area when touched induces pain. Based on this information, the doctor can draw a conclusion and reach a diagnosis regarding the patient's medical condition or injury.

The technology can also be used to establish a channel of two-way touch communication. As opposed to drawing a medical prognosis from a patient's verbal response, doctors often have to assess a patient's medical state by examining his or her physical attributes. For example, if a doctor wanted to examine a patient's throat to check if his or her tonsils were inflamed or swollen, the doctor could do you by placing his fingers on the area of the doll that corresponds to the patient's throat. The doll would then translate that information through the internet just as if it was a one-way channel of touch, and would then be output through the pressure chips embedded in the jacket. In order to assess the shape or the condition of the patient's tonsils, the response that the tonsils will have in response to the pressure applied will be recorded. By measuring the elasticity and the plasticity the tissue exhibits, one can determine if it is swollen beyond its normal state. This information can be relayed through either a computer that simply reports that the tissue is swollen or presents an image of what the tonsils would look like based on its structural integrity, or it can be manifested through the doll by altering its throat to emulate the shape and feel of the patient's throat.

Another method of communicating the gesture of touch is through a motion detection technology. Instead of pinpointing the area of contact you want to establish by touching a doll or dummy, the motion detection technology can gather hand motions to determine what kind of touching motion to simulate, and will then utilize the jacket to illicit the targeted sensation of touch.

In one embodiment, the interaction is one-way. In one embodiment of a two-way interaction shown in FIG. 18, the vest itself is able to identify conditions of the body to the SWAP platform. This information can be translated to a remote physical diagnosis. The firmness and strength of a material can easily be diagnosed. The jacket can also be used to record basic vital signs. One embodiment relates to creating a tactile aspect to the interaction wherein the patient could respond verbally.

SWAP Health Platform For Pets

SWAP communication platform can be used for remote diagnosis, treatment, monitoring, and notification of pets by veterinary health care providers. SWAP health platform can be used for the following scenarios.

Pet owners can consult veterinary health care personnel to diagnose a sick pet by using SWAP's multimedia collaboration platforms. Pet owners will be able to show their sick pets to a veterinary doctor over the video communication channel.

A sick pet's health vitals can be monitored using monitoring devices that transmit continuously data to SWAP system. This data can be compared with short term and long term health data of the pet and any abnormal conditions can be detected automatically and owners can be alerted.

Owners of sick pets can monitor their condition of pet through SWAP platform when they are away from home.

In addition, using SWAP's touch sensors, owners can remotely create a hugging sensation which can be extremely helpful when the owners are away from their pets for an extended period of time.

APPENDIX 1

The U.S. patents and publications listed below are hereby incorporated herein by reference in their entirety. U.S. Pat. No. 8,102,406; Issue date: Jan. 24, 2102; Method and system for producing a video synopsis, U.S. Pat. No. 8,073,839; Issue date: Dec. 6, 2011; System and method of peer to peer searching, sharing, social networking and communication in one or more networks, U.S. Pat. No. 7,523,163; Issue date:

Apr. 21, 2009; Distributed network system architecture for collaborative computing, U.S. Pat. No. 7,313,595; Issue date: Dec. 25, 2007; System and method for record and playback of collaborative web browsing session, U.S. Pat. No. 7,236,926; Issue date: Jun. 26, 2007; System and method for voice transmission over network protocols, U.S. Pat. No. 6,567,813; Issue date: May 20, 2003; Quality of service maintenance for distributed collaborative computing, Publication number: US 2011/0258125; Filing date: Apr. 14, 2011; Collaborative social event planning and execution, Publication number: US 2011/0225519; Filing date: Feb. 16, 2011 Social media platform for simulating a live experience, Publication number: US 2011/0066664; Filing date: Sep. 15, 2010; Sports collaboration and communication platform, Publication number: US 2010/0299334; Filing date: Sep. 8, 2009; Computer implemented system and method for providing a community and collaboration platform around knowledge transfer, expertise, innovation, tangible assets, intangible assets and information assets, Publication number: US 2010/0332616; Filing date: Aug. 31, 2009; Web guide, Publication number: US 2010/0262550; Filing date: Apr. 8, 2009; Inter-corporate collaboration overlay solution for professional social networks, Publication number: US 2009/0094039; Filing date: Oct. 4, 2007; Collaborative production of rich media content, Publication number: US 2008/0297588; Filing date: May 31, 2007, Managing scene transitions for video communication, Publication number: US 2005/0198141; Filing date: Feb. 4, 2005; Secure communications system for collaborative computing, Publication number: US 2003/0167304; Filing date: Dec. 29, 2000; Distributed meeting management, Publication number: US 2003/0164853; Filing date: Dec. 29, 2000; Distributed document sharing, Publication number: US 2013/0046149; Filing date: Aug. 19, 2011; Interactive virtual care, Publication number: US 2004/0059603; Filing date: Apr. 15, 2003; System and method for virtual health services, Publication number: US 2002/0065682; Filing date: May 18, 1999; Virtual Doctor Interactive Cybernet System, U.S. Pat. No. 8,321,284; Issue date: Nov. 27, 2012; System, method, and program product for delivering medical services from a remote location, Publication number: US 2004/0235446; Filing date: Jun. 14, 2004; Medical apparatus remote control and method, Publication No. US2012/0259648; Filing date: Apr. 7, 2011; Systems and methods for remote monitoring, management and optimization of physical therapy treatment.

What is claimed is:

1. A system comprising:
   a pair of devices to enable communication between a first person and a second person;
   a body-suit to be worn by the first person, the body-suit comprising one or more actuators configured to convert electrical signals to tactile stimuli and/or electrical stimuli, wherein the body-suit is configured to convey the tactile stimuli and/or the electrical stimuli to a body part of the first person in response to a pressure applied; and
   a model replica of the body-suit configured to receive the tactile stimuli and/or the electrical stimuli from the second person for the pressure applied and to convert the tactile stimuli and/or the electrical stimuli into the electrical signals which are conveyed to the body-suit over a network;
   wherein a computing device is configured to modify a physical structure of the model replica to emulate a shape and a feel of a region of the body part of the first person;
   wherein the body-suit is configured to replicate the tactile stimuli and/or the electrical stimuli of the model replica and convey the tactile stimuli and/or the electrical stimuli to the first person; and
   wherein the system allows the second person to send a physical sensation of touch remotely to the first person.

2. The system of claim 1, wherein the communication includes a physical response of the first person to the tactile stimuli and/or the electrical stimuli, the physical response enabling the second person to determine a physical and/or a mental state of the first person.

3. The system of claim 2, wherein the physical response is either verbal or visual.

4. The system of claim 1, wherein the body-suit is configured to cover one or more of arms, torso, neck, throat, legs, hands and feet of the first person.

5. The system of claim 1, wherein the system allows transmission of two-way touch sensation between the first person and the second person.

6. The system of claim 1, wherein the system allows for tactile interfacing utilizing a visual communication channel and an auditory communication channel.

7. The system of claim 2, wherein the physical response further enables the second person to moderate the tactile stimuli.

8. The system of claim 1, wherein the body-suit comprises a jacket.

9. The system of claim 1, wherein the model replica comprises a doll or dummy.

10. The system of claim 1, wherein the communication between the first person and the second person comprises a one-way communication or a two-way communication.

11. The system of claim 1, wherein the tactile stimuli and/or the electrical stimuli consists of the tactile stimuli.

12. The system of claim 1, wherein the tactile stimuli and/or the electrical stimuli consists of the electrical stimuli.

13. The system of claim 1, wherein the second person conveys the tactile stimuli and/or the electrical stimuli to the first person by placing one or more fingers of the second person on the model replica.

14. The system of claim 1, wherein the body-suit is configured to convey mechanical stimuli to the body part of the first person.

15. The system of claim 1, wherein the system is configured to communicate a gesture of touch via a motion detection technology that gathers hand motions to determine a touching motion.

16. The system of claim 1, wherein the computing device comprises a tablet, a computer, a laptop, a cell phone or a combination thereof.

17. The system of claim 1, wherein the body-suit comprises touch sensitive chips that stimulate a particular area of skin to create a sensation of touch.

18. The system of claim 1, wherein certain information related to touching a certain area on the model replica is sent over the network comprising Internet, the body-suit receives the certain information and the body-suit translates the certain information into an electrical impulse that models the physical sensation of touch.

* * * * *